(12) United States Patent
Cully et al.

(10) Patent No.: US 9,204,887 B2
(45) Date of Patent: Dec. 8, 2015

(54) DEVICES AND SYSTEMS FOR THROMBUS TREATMENT

(71) Applicant: W. L. Gore & Associates, Inc., Newark, DE (US)

(72) Inventors: Edward H. Cully, Flagstaff, AZ (US); Nathan L. Friedman, Flagstaff, AZ (US); Eric H. Zacharias, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 142 days.

(21) Appl. No.: 13/802,428

(22) Filed: Mar. 13, 2013

(65) Prior Publication Data
US 2014/0052103 A1 Feb. 20, 2014

Related U.S. Application Data

(60) Provisional application No. 61/683,043, filed on Aug. 14, 2012.

(51) Int. Cl.
| | | |
|---|---|---|
| A61B 17/221 | (2006.01) | |
| A61M 25/00 | (2006.01) | |
| A61F 2/01 | (2006.01) | |

(Continued)

(52) U.S. Cl.
CPC ....... *A61B 17/221* (2013.01); *A61B 17/320725* (2013.01); *A61F 2/013* (2013.01); *A61M 25/00* (2013.01); *A61B 2017/22069* (2013.01); *A61F 2002/018* (2013.01)

(58) Field of Classification Search
CPC . A61B 17/221; A61M 25/00; A61F 2002/011

USPC .......... 606/110, 114, 127, 128, 159
See application file for complete search history.

(56) References Cited

U.S. PATENT DOCUMENTS

| | | | |
|---|---|---|---|
| 4,374,026 | A | 2/1983 | Greutert |
| 4,425,908 | A | 1/1984 | Simon |
| 4,643,184 | A | 2/1987 | Mobin-Uddin |

(Continued)

FOREIGN PATENT DOCUMENTS

| | | |
|---|---|---|
| DE | 29916162 | 1/2000 |
| EP | 0472334 | 2/1992 |

(Continued)

OTHER PUBLICATIONS

European Search Report for Application No. EP 10011979, dated Oct. 17, 2011, 5 pages.

(Continued)

*Primary Examiner* — Todd Manahan
*Assistant Examiner* — Casey B Lewis
(74) *Attorney, Agent, or Firm* — Katherine L. Carleton

(57) ABSTRACT

A thrombus treatment device includes a support wire, a body frame portion that is disposed about an axis defined by the support wire, one or more tethers that each have a first end and a second end, and a filter element extending from the body frame portion. Each of the one or more tethers is attached at its first end to the body frame portion, and at its second end to a collar that couples the second end of each of the multiple tethers to the support wire. When the collar is positioned substantially within a region interior of the body frame portion, a rotational actuation of the support wire causes a swiveling motion of the one or more tethers.

26 Claims, 13 Drawing Sheets

(51) Int. Cl.
*A61B 17/3207* (2006.01)
*A61B 17/22* (2006.01)

(56) References Cited

U.S. PATENT DOCUMENTS

| | | | |
|---|---|---|---|
| 4,690,672 A | 9/1987 | Veltrup |
| 4,706,671 A | 11/1987 | Weinrib |
| 4,723,549 A | 2/1988 | Wholey et al. |
| 5,011,488 A | 4/1991 | Ginsburg |
| 5,100,423 A | 3/1992 | Fearnot |
| 5,102,415 A | 4/1992 | Guenther et al. |
| 5,133,733 A | 7/1992 | Rasmussen et al. |
| 5,192,286 A | 3/1993 | Phan et al. |
| 5,211,651 A | 5/1993 | Reger et al. |
| 5,370,609 A | 12/1994 | Drasler et al. |
| 5,419,774 A | 5/1995 | Willard et al. |
| 5,495,519 A | 2/1996 | Chen |
| 5,634,942 A | 6/1997 | Chevillon et al. |
| 5,688,234 A | 11/1997 | Frisbie |
| 5,695,518 A | 12/1997 | Laerum |
| 5,695,519 A | 12/1997 | Summers et al. |
| 5,709,704 A | 1/1998 | Nott et al. |
| 5,735,892 A | 4/1998 | Myers et al. |
| 5,769,816 A | 6/1998 | Barbut et al. |
| 5,785,675 A | 7/1998 | Drasler et al. |
| 5,814,064 A | 9/1998 | Daniel et al. |
| 5,827,324 A | 10/1998 | Cassell et al. |
| 5,833,650 A | 11/1998 | Imran |
| 5,853,420 A | 12/1998 | Chevillon et al. |
| 5,876,367 A | 3/1999 | Kaganov et al. |
| 5,893,869 A | 4/1999 | Barnhart et al. |
| 5,902,475 A | 5/1999 | Trozera et al. |
| 5,907,893 A | 6/1999 | Zadno-Azizi et al. |
| 5,908,435 A | 6/1999 | Samuels |
| 5,910,154 A | 6/1999 | Tsugita et al. |
| 5,911,734 A | 6/1999 | Tsugita et al. |
| 5,941,869 A | 8/1999 | Patterson et al. |
| 5,941,871 A | 8/1999 | Adams et al. |
| 5,941,896 A | 8/1999 | Kerr |
| 5,971,938 A | 10/1999 | Hart et al. |
| 5,980,552 A | 11/1999 | Pinchasik et al. |
| 5,980,555 A | 11/1999 | Barbut et al. |
| 5,989,271 A | 11/1999 | Bonnette et al. |
| 5,989,281 A | 11/1999 | Barbut et al. |
| 6,001,118 A | 12/1999 | Daniel et al. |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,058,914 A | 5/2000 | Suzuki |
| 6,059,814 A | 5/2000 | Ladd |
| 6,066,149 A | 5/2000 | Samson et al. |
| 6,068,645 A | 5/2000 | Tu |
| 6,074,357 A | 6/2000 | Kaganov et al. |
| 6,080,170 A | 6/2000 | Nash et al. |
| 6,083,215 A | 7/2000 | Milavetz |
| 6,090,097 A | 7/2000 | Barbut et al. |
| 6,091,980 A | 7/2000 | Squire et al. |
| 6,096,001 A | 8/2000 | Drasler et al. |
| 6,099,549 A | 8/2000 | Bosma et al. |
| 6,117,154 A | 9/2000 | Barbut et al. |
| 6,129,739 A | 10/2000 | Khosravi |
| 6,135,977 A | 10/2000 | Drasler et al. |
| 6,136,016 A | 10/2000 | Barbut et al. |
| 6,142,987 A | 11/2000 | Tsugita |
| 6,146,370 A | 11/2000 | Barbut |
| 6,152,946 A | 11/2000 | Broome et al. |
| 6,152,947 A | 11/2000 | Ambrisco et al. |
| 6,168,603 B1 | 1/2001 | Leslie et al. |
| 6,168,604 B1 | 1/2001 | Cano |
| 6,168,622 B1 | 1/2001 | Mazzocchi |
| 6,171,327 B1 | 1/2001 | Daniel et al. |
| 6,171,328 B1 | 1/2001 | Addis |
| 6,171,329 B1 | 1/2001 | Shaw et al. |
| 6,176,844 B1 | 1/2001 | Lee |
| 6,179,859 B1 | 1/2001 | Bates et al. |
| 6,187,025 B1 | 2/2001 | Machek |
| 6,203,561 B1 | 3/2001 | Ramee et al. |
| 6,206,868 B1 | 3/2001 | Parodi |
| 6,214,025 B1 | 4/2001 | Thistle et al. |
| 6,221,006 B1 | 4/2001 | Dubrul et al. |
| 6,224,612 B1 | 5/2001 | Bates et al. |
| 6,231,544 B1 | 5/2001 | Tsugita et al. |
| 6,231,589 B1 | 5/2001 | Wessman et al. |
| 6,235,045 B1 | 5/2001 | Barbut et al. |
| 6,238,412 B1 | 5/2001 | Dubrul et al. |
| 6,245,089 B1 | 6/2001 | Daniel et al. |
| 6,258,061 B1 | 7/2001 | Drasler et al. |
| 6,258,115 B1 | 7/2001 | Dubrul et al. |
| 6,264,672 B1 | 7/2001 | Fisher |
| 6,277,139 B1 | 8/2001 | Levinson et al. |
| 6,290,710 B1 | 9/2001 | Cryer et al. |
| 6,325,815 B1 | 12/2001 | Kusleika et al. |
| 6,325,816 B1 | 12/2001 | Fulton, III et al. |
| 6,327,772 B1 | 12/2001 | Zadno-Azizi et al. |
| 6,338,735 B1 | 1/2002 | Stevens |
| 6,346,116 B1 | 2/2002 | Brooks et al. |
| 6,346,117 B1 | 2/2002 | Greenhalgh |
| 6,361,546 B1 | 3/2002 | Khosravi et al. |
| 6,364,895 B1 | 4/2002 | Greenhalgh |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,391,037 B1 | 5/2002 | Greenhalgh |
| 6,391,044 B1 | 5/2002 | Yadav et al. |
| 6,403,535 B1 | 6/2002 | Muller et al. |
| 6,432,122 B1 | 8/2002 | Gilson et al. |
| 6,436,120 B1 | 8/2002 | Meglin |
| 6,443,972 B1 | 9/2002 | Bosma et al. |
| 6,447,531 B1 | 9/2002 | Amplatz |
| 6,450,989 B2 | 9/2002 | Dubrul et al. |
| 6,485,500 B1 | 11/2002 | Kokish et al. |
| 6,485,501 B1 | 11/2002 | Green |
| 6,485,502 B2 | 11/2002 | Michael et al. |
| 6,491,660 B2 | 12/2002 | Guo et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,517,551 B1 | 2/2003 | Driskill |
| 6,517,559 B1 | 2/2003 | O'Connell |
| 6,524,323 B1 | 2/2003 | Nash et al. |
| 6,527,746 B1 | 3/2003 | Oslund et al. |
| 6,540,722 B1 | 4/2003 | Boyle et al. |
| 6,544,209 B1 | 4/2003 | Drasler et al. |
| 6,544,276 B1 | 4/2003 | Azizi |
| 6,544,279 B1 | 4/2003 | Hopkins et al. |
| 6,558,405 B1 | 5/2003 | McInnes |
| 6,575,996 B1 | 6/2003 | Denison et al. |
| 6,599,307 B1 | 7/2003 | Huter et al. |
| 6,605,102 B1 | 8/2003 | Mazzocchi et al. |
| 6,610,077 B1 | 8/2003 | Hancock et al. |
| 6,635,070 B2 | 10/2003 | Leeflang et al. |
| 6,652,548 B2 | 11/2003 | Evans et al. |
| 6,660,021 B1 | 12/2003 | Palmer et al. |
| 6,676,637 B1 | 1/2004 | Bonnette et al. |
| 6,679,893 B1 | 1/2004 | Tran |
| 6,682,546 B2 | 1/2004 | Amplatz |
| 6,695,813 B1 | 2/2004 | Boyle et al. |
| 6,695,858 B1 | 2/2004 | Dubrul et al. |
| 6,695,865 B2 | 2/2004 | Boyle et al. |
| 6,712,835 B2 | 3/2004 | Mazzocchi et al. |
| 6,716,231 B1 | 4/2004 | Rafiee et al. |
| 6,726,701 B2 | 4/2004 | Gibson et al. |
| 6,730,117 B1 | 5/2004 | Tseng et al. |
| 6,740,061 B1 | 5/2004 | Oslund et al. |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,805,684 B2 | 10/2004 | Bonnette et al. |
| 6,814,740 B2 | 11/2004 | McAlister |
| 6,887,256 B2 | 5/2005 | Gibson et al. |
| 6,890,340 B2 | 5/2005 | Duane |

(56) References Cited

U.S. PATENT DOCUMENTS

| | | |
|---|---|---|
| 6,939,361 B1 | 9/2005 | Kleshinski |
| 6,939,362 B2 | 9/2005 | Boyle et al. |
| 6,986,778 B2 | 1/2006 | Zadno-Azizi |
| 6,989,019 B2 | 1/2006 | Mazzocchi et al. |
| 7,011,654 B2 | 3/2006 | Dubrul et al. |
| 7,163,550 B2 | 1/2007 | Boismier |
| 7,214,237 B2 | 5/2007 | Don Michael et al. |
| 7,220,269 B1 | 5/2007 | Ansel et al. |
| 7,229,462 B2 | 6/2007 | Sutton et al. |
| 7,229,463 B2 | 6/2007 | Sutton et al. |
| 7,241,304 B2 | 7/2007 | Boyle et al. |
| 7,241,305 B2 | 7/2007 | Ladd |
| 7,252,675 B2 | 8/2007 | Denison et al. |
| 7,306,618 B2 | 12/2007 | Demond et al. |
| 7,338,510 B2 | 3/2008 | Boylan et al. |
| 7,344,549 B2 | 3/2008 | Boyle et al. |
| 7,399,308 B2 | 7/2008 | Borillo et al. |
| 7,491,210 B2 | 2/2009 | Dubrul et al. |
| 7,537,601 B2 | 5/2009 | Cano et al. |
| 7,717,936 B2 | 5/2010 | Keating et al. |
| 7,766,936 B2 | 8/2010 | Ladd |
| 7,780,694 B2 | 8/2010 | Palmer et al. |
| 7,785,345 B2 | 8/2010 | Ladd |
| 7,942,892 B2 | 5/2011 | D'Aquanni et al. |
| 8,070,769 B2 | 12/2011 | Broome |
| 8,088,140 B2 | 1/2012 | Ferrera et al. |
| 8,109,962 B2 * | 2/2012 | Pal ..................... 606/200 |
| 8,231,650 B2 * | 7/2012 | Cully et al. ............. 606/200 |
| 8,252,017 B2 | 8/2012 | Paul, Jr. et al. |
| 8,313,503 B2 | 11/2012 | Cully et al. |
| 8,337,520 B2 | 12/2012 | Cully et al. |
| 8,597,322 B2 | 12/2013 | Cully et al. |
| 8,801,750 B2 | 8/2014 | Cully et al. |
| 2001/0044634 A1 | 11/2001 | Don Michael et al. |
| 2001/0044652 A1 | 11/2001 | Moore |
| 2002/0022858 A1 | 2/2002 | Demond et al. |
| 2002/0026203 A1 | 2/2002 | Bates et al. |
| 2002/0038767 A1 | 4/2002 | Trozera |
| 2002/0058911 A1 | 5/2002 | Gilson et al. |
| 2002/0068954 A1 | 6/2002 | Foster |
| 2002/0088531 A1 | 7/2002 | Cook et al. |
| 2002/0091408 A1 | 7/2002 | Sutton et al. |
| 2002/0091409 A1 | 7/2002 | Sutton et al. |
| 2002/0111648 A1 | 8/2002 | Kusleika et al. |
| 2002/0123720 A1 | 9/2002 | Kusleika et al. |
| 2002/0138094 A1 | 9/2002 | Borillo et al. |
| 2003/0045898 A1 | 3/2003 | Harrison et al. |
| 2003/0060844 A1 | 3/2003 | Borillo et al. |
| 2003/0065354 A1 | 4/2003 | Boyle et al. |
| 2003/0065355 A1 | 4/2003 | Weber |
| 2003/0120303 A1 | 6/2003 | Boyle et al. |
| 2003/0139764 A1 | 7/2003 | Levinson et al. |
| 2003/0144688 A1 | 7/2003 | Brady et al. |
| 2003/0153943 A1 | 8/2003 | Michael et al. |
| 2003/0187474 A1 | 10/2003 | Keegan et al. |
| 2003/0187495 A1 | 10/2003 | Cully et al. |
| 2003/0208224 A1 | 11/2003 | Broome |
| 2003/0229374 A1 | 12/2003 | Brady et al. |
| 2004/0093012 A1 | 5/2004 | Cully et al. |
| 2004/0215230 A1 | 10/2004 | Frazier et al. |
| 2005/0101989 A1 | 5/2005 | Cully et al. |
| 2005/0177186 A1 | 8/2005 | Cully et al. |
| 2005/0192620 A1 | 9/2005 | Cully et al. |
| 2006/0015136 A1 | 1/2006 | Besselink |
| 2006/0030877 A1 | 2/2006 | Martinez et al. |
| 2006/0135987 A1 | 6/2006 | Jones et al. |
| 2006/0241676 A1 | 10/2006 | Johnson et al. |
| 2006/0253145 A1 | 11/2006 | Lucas et al. |
| 2007/0060942 A2 | 3/2007 | Zadno-Azizi |
| 2007/0088383 A1 | 4/2007 | Pal et al. |
| 2007/0112374 A1 | 5/2007 | Paul, Jr. et al. |
| 2007/0191878 A1 | 8/2007 | Segner et al. |
| 2007/0198051 A1 | 8/2007 | Clubb et al. |
| 2007/0208351 A1 | 9/2007 | Turner et al. |
| 2008/0152367 A1 | 6/2008 | Wayman |
| 2008/0234722 A1 | 9/2008 | Bonnette et al. |
| 2008/0312681 A1 | 12/2008 | Ansel et al. |
| 2009/0326575 A1 | 12/2009 | Galdonik et al. |
| 2010/0268264 A1 | 10/2010 | Bonnette et al. |
| 2010/0286722 A1 * | 11/2010 | Rizk et al. ................. 606/200 |
| 2011/0040314 A1 | 2/2011 | McGuckin et al. |
| 2011/0184456 A1 | 7/2011 | Grandfield et al. |
| 2012/0289997 A1 | 11/2012 | Cully et al. |
| 2013/0144327 A1 | 6/2013 | Cully et al. |
| 2013/0184737 A1 | 7/2013 | Cully et al. |
| 2013/0197566 A1 | 8/2013 | Cully et al. |
| 2013/0289589 A1 | 10/2013 | Krolik et al. |
| 2014/0018842 A1 | 1/2014 | Cully et al. |
| 2014/0052161 A1 | 2/2014 | Cully |

FOREIGN PATENT DOCUMENTS

| | | |
|---|---|---|
| EP | 655228 | 11/1994 |
| EP | 1179321 | 2/2002 |
| EP | 812155 | 12/2003 |
| EP | 1566148 | 8/2005 |
| EP | 1545388 | 5/2009 |
| FR | 2580504 | 10/1986 |
| FR | 2694687 | 2/1994 |
| GB | 2337002 | 11/1999 |
| JP | 8-187294 | 7/1996 |
| JP | 2002505151 | 2/2002 |
| JP | 2002526496 | 8/2002 |
| JP | 2004538097 | 12/2004 |
| WO | 98/33443 | 8/1998 |
| WO | 9915224 | 4/1999 |
| WO | 99/22673 | 5/1999 |
| WO | 99/23976 | 5/1999 |
| WO | 99/25252 | 5/1999 |
| WO | 99/44542 | 9/1999 |
| WO | 00/16705 | 3/2000 |
| WO | 00/49970 | 8/2000 |
| WO | 00/07521 | 9/2000 |
| WO | 00/53120 | 9/2000 |
| WO | 00/67665 | 11/2000 |
| WO | 01/08595 | 2/2001 |
| WO | 01/15629 | 3/2001 |
| WO | 01/19231 | 3/2001 |
| WO | 01/19260 | 3/2001 |
| WO | 0117602 | 3/2001 |
| WO | 01/45569 | 6/2001 |
| WO | 0145590 | 6/2001 |
| WO | 01/49215 | 7/2001 |
| WO | 0152768 | 7/2001 |
| WO | 0158382 | 8/2001 |
| WO | 0167989 | 9/2001 |
| WO | 03/011188 | 2/2003 |
| WO | 03/017823 | 3/2003 |
| WO | 03/035130 | 5/2003 |
| WO | 03/055412 | 7/2003 |
| WO | 03/063732 | 8/2003 |
| WO | 03/077799 | 9/2003 |
| WO | 2004/034884 | 4/2004 |
| WO | 2008/036156 | 3/2008 |
| WO | WO 2013/071173 A1 * | 3/2012 ............ A61B 17/22 |

OTHER PUBLICATIONS

European Search Report for EP Application No. 03809115.3, completed Apr. 24, 2008, 2 pages.

European Search Report for EP13184820, mailed Feb. 28, 2014, 5 pages.

International Preliminary Examination Report for PCT/US2003/032962, mailed Mar. 15, 2005, 3 pages.

Partial European Search Report for Application No. EP 10011979, dated Apr. 19, 2011, 4 pages.

International Search Report for PCT/US2013/053647 mailed Oct. 29, 2013, corresponding to U.S. Appl. No. 13/802,428, 6 pgs.

International Search Report for PCT/US2013/053655 mailed Oct. 10, 2013, corresponding to U.S. Appl. No. 13/802,437, 6 pgs.

Alligator Retrieval Device (ARD), Chestnut Medical Technologies, Inc. Instructional Guide (www.chestnutmedical.com).

(56) References Cited

OTHER PUBLICATIONS

Bamford J, et al. Incidence of Stroke in Oxfordshre: First Year's Experience of a Community Stroke Register. British Medical Journal 1983;287:713-717.
Barnett et al. Beneficial Effect of Carotid Endarterectomy, NE Journal of Medicine 1991; 325(7):446-453.
European Search Report, EP Application No. EP09007542, Jul. 28, 2009, Munich, 4 pages.
Executive Committee for the Endarterectomy for Asymptomatic Carotid Atherosclerosis Study. Endarterectomy for Asymptomatic Carotid Artery Stenosis. JAMA 1995;273(18): 1421-1461.
Gunther RW and Vorwerk D., Minibasket for Percutaneous Embolectomy and Filter Protection Against Distal Embolization: Technical Note. Cardiovasc Intervent Radiol 1991; 14:195-98.
Hankey GJ Investigation and Imaging Strategies in Acute Stroke and Transient Ischaemic Attacks. Hospital Update 1992; 107-124.
International Search Report and Written Opinion for PCT/US03/32962 (WO04/034884), mailed Apr. 14, 2004, 8 pages.
International Search Report Dated Dec. 12, 2009 from Corresponding International Application PCT/US08/66644.
Report on Patentability Dated Dec. 17, 2009 from Corresponding International Application PCT/US08/66644.
Robins M, et al. The National Survey of Stroke: The National Institute of Neurological and Communicative Disorders and Stroke. Office of Biometry and Field Studies Report. Chapter 4. Incidence. Stroke 1981; Part II; 12(2):I-45 to I-57.
Search Report Dated Aug. 26, 2006 From Corresponding EP Patent No. 1696966.
Theron J et al. 1990 New Triple Coaxial Catheter System for Carotid Angioplasty with Cerebral Protection. Amer J of Neuroradiology 1990; 11:869-874.
Theron J G et al. 1996 Carotid Artery Stenosis: Treatment with Protected Balloon Angioplasty and Stent Placement. Radiology 1996; 201:627-636.
Yadav JS et al. Elective Stenting of the Extracranial Carotid Arteries. Circulation 1997; 95:376-381.

* cited by examiner

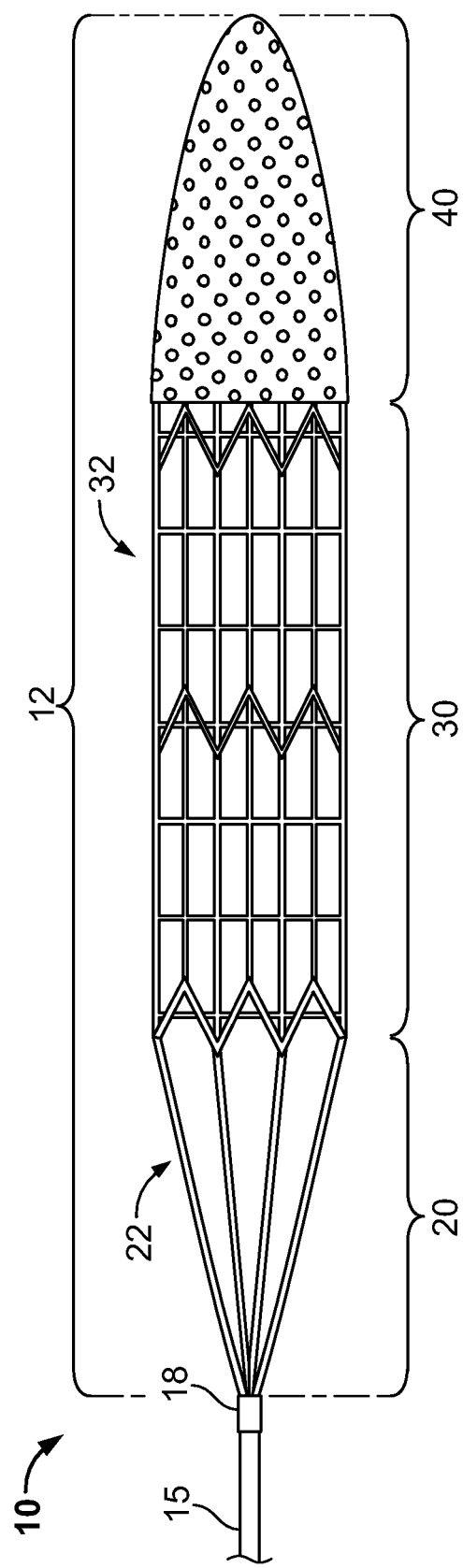

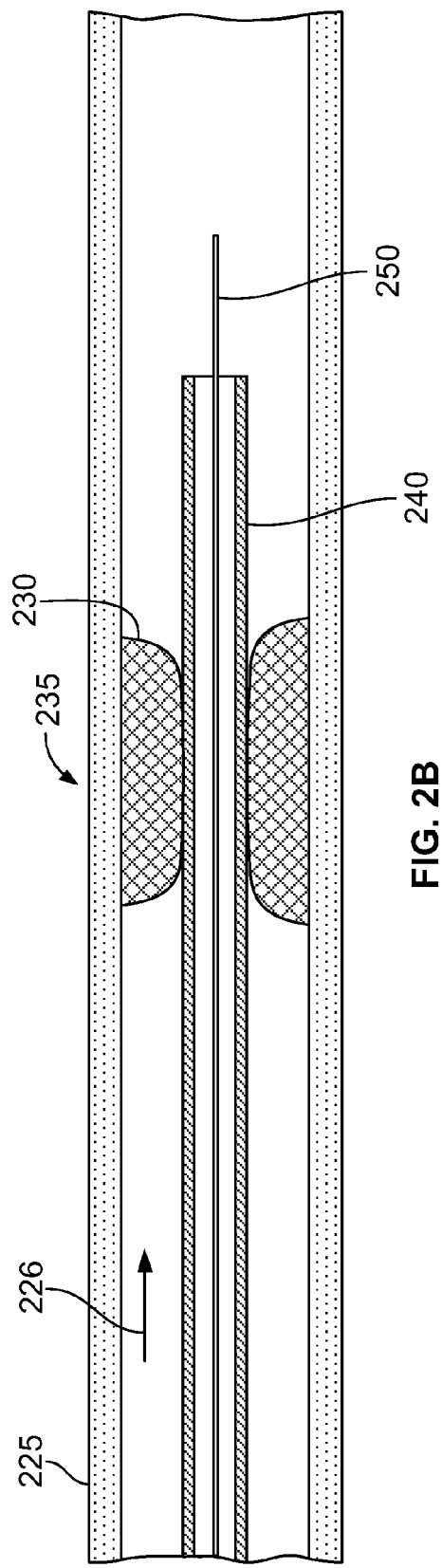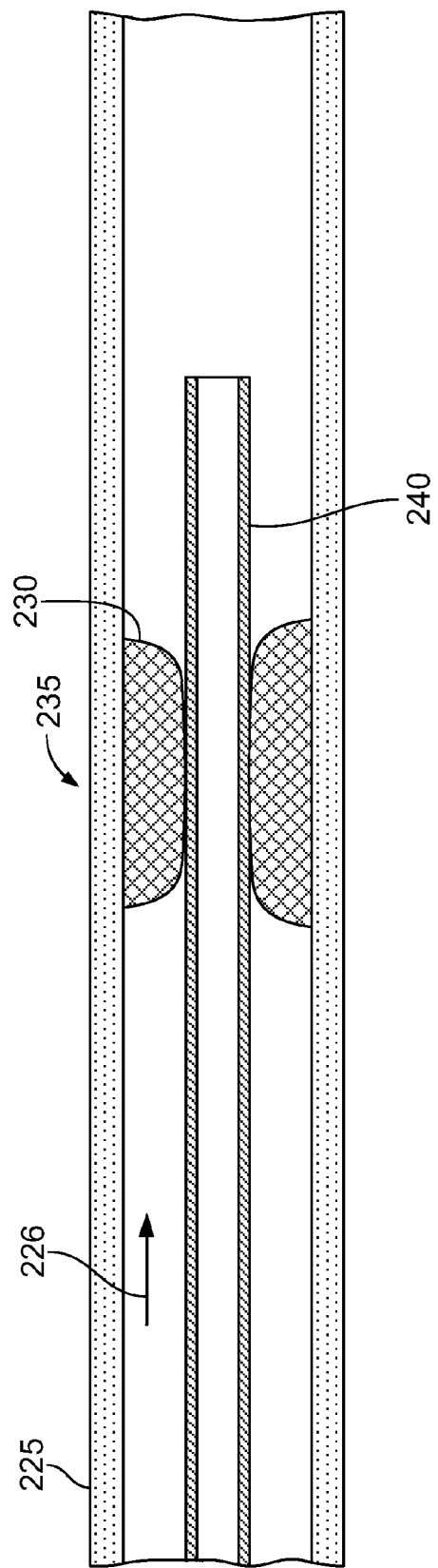

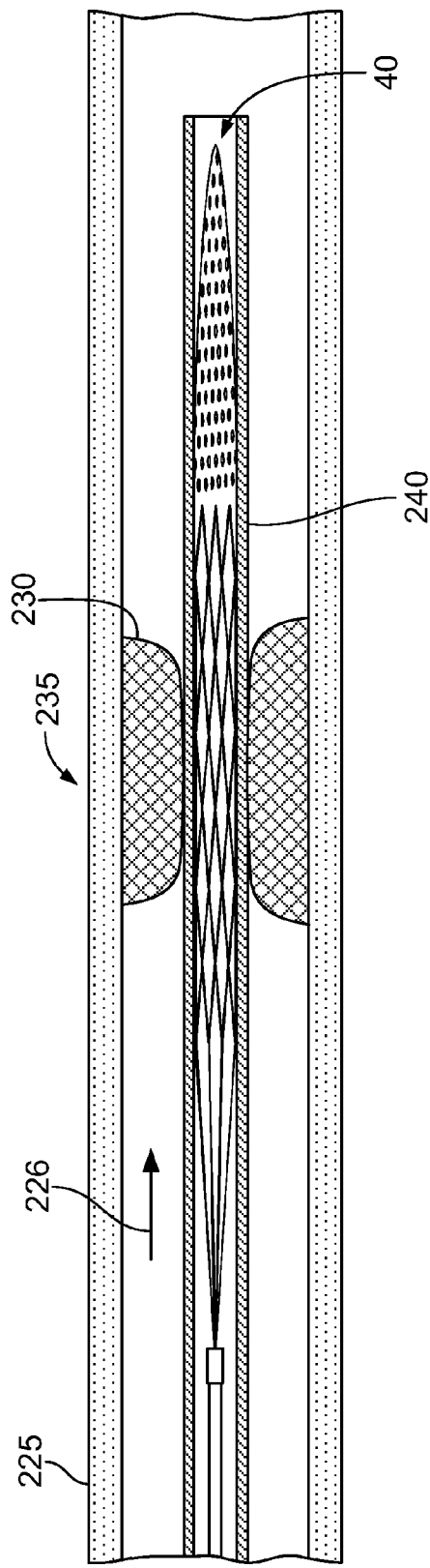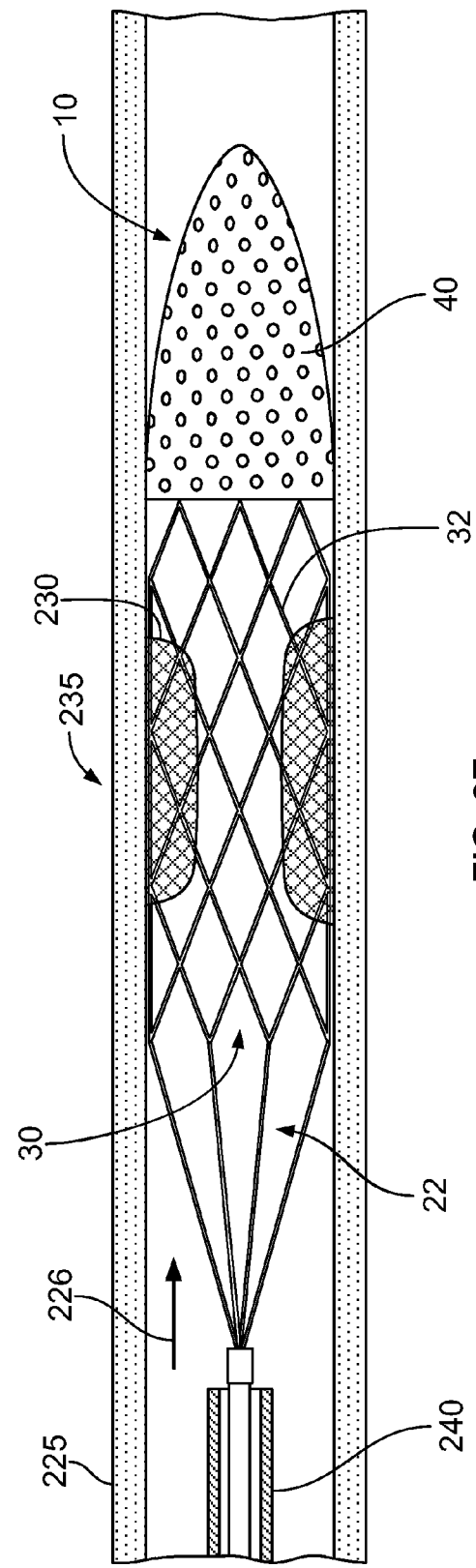

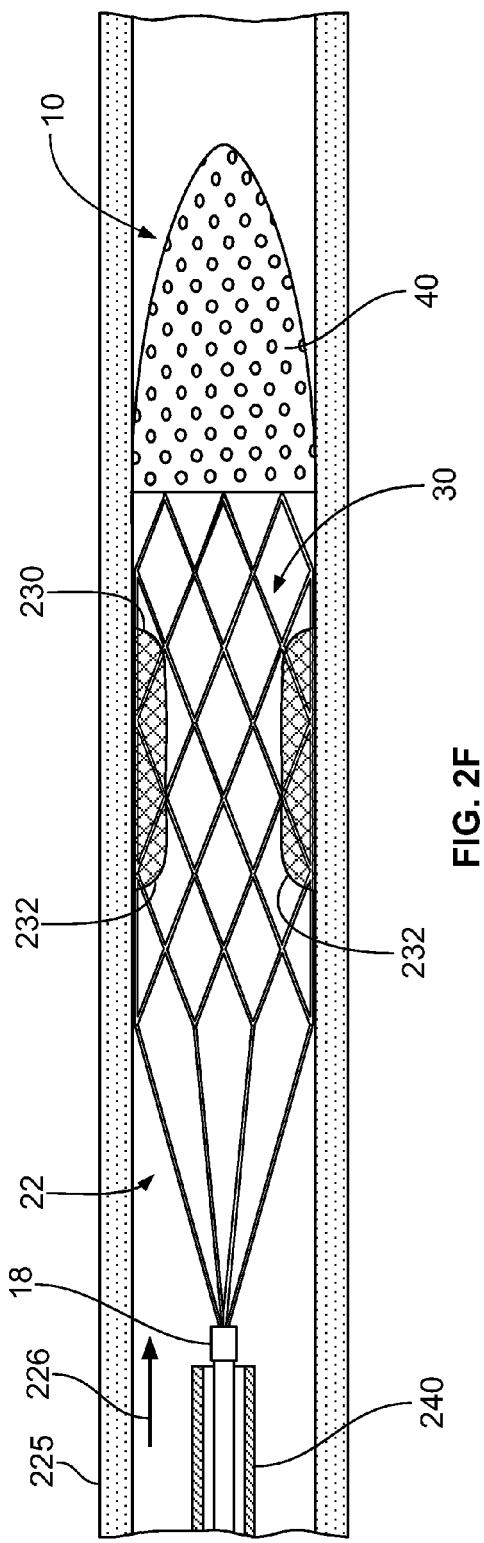
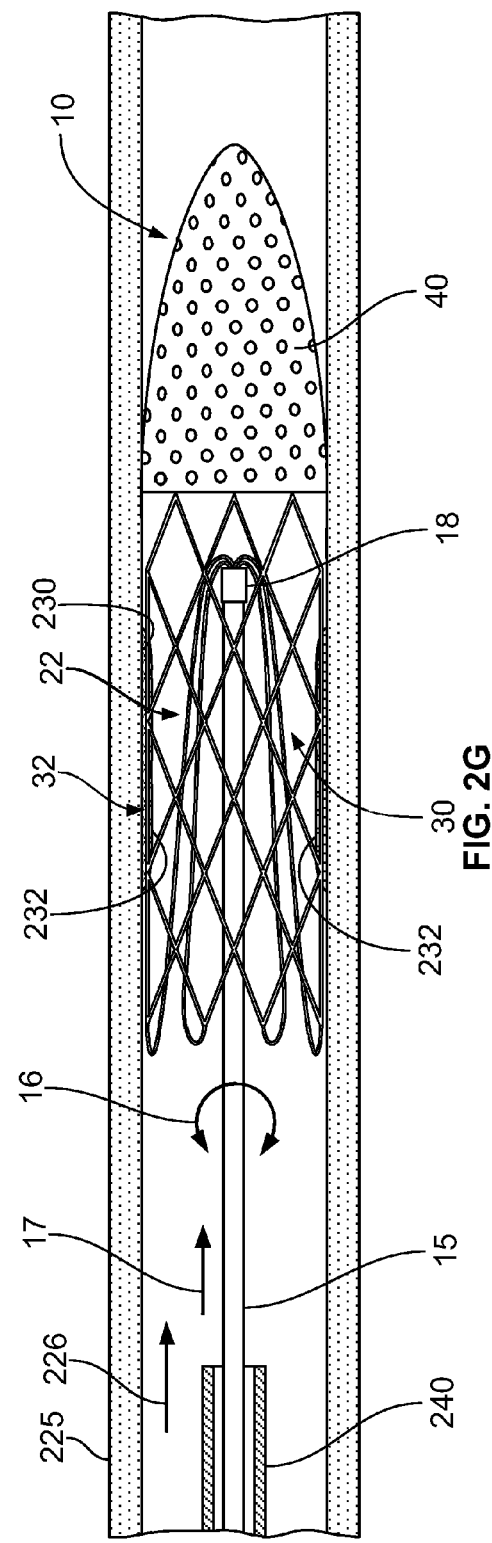

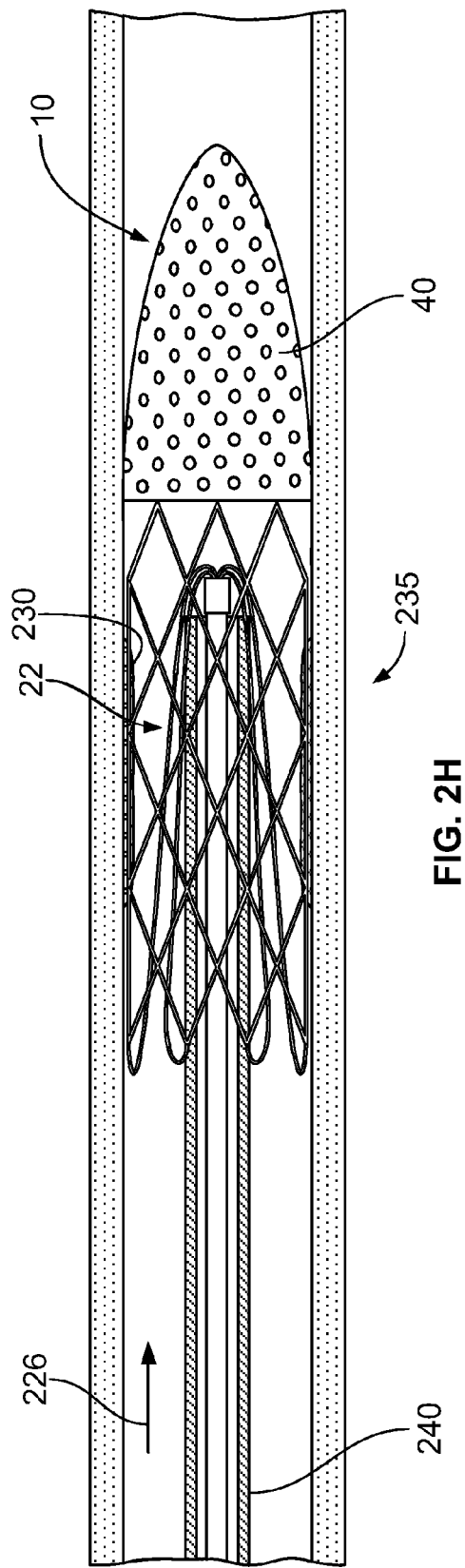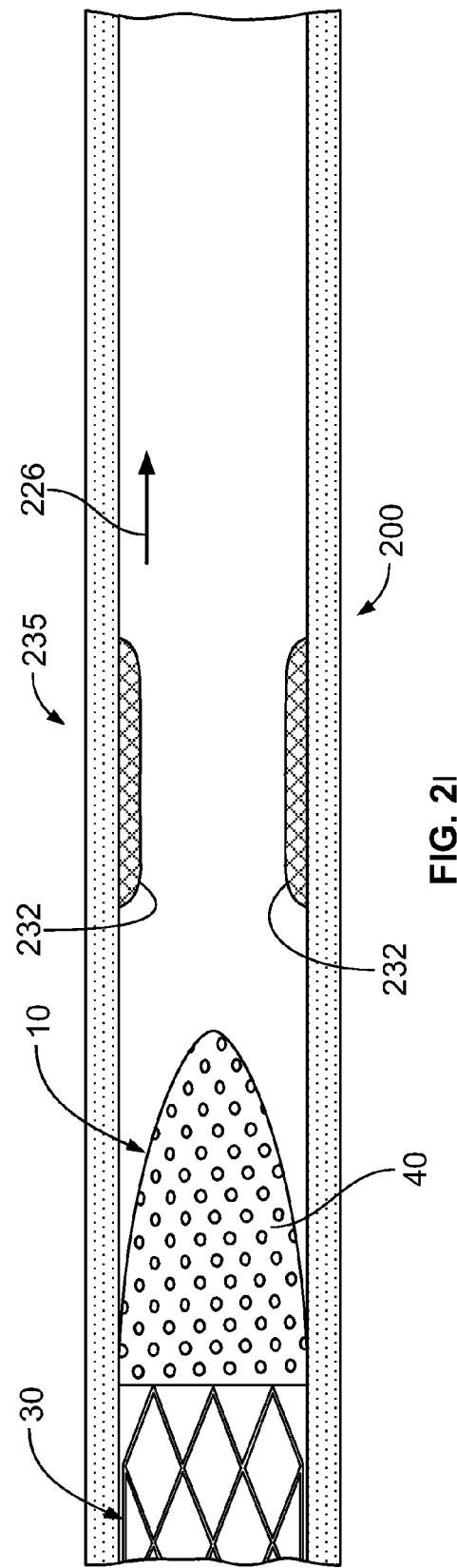

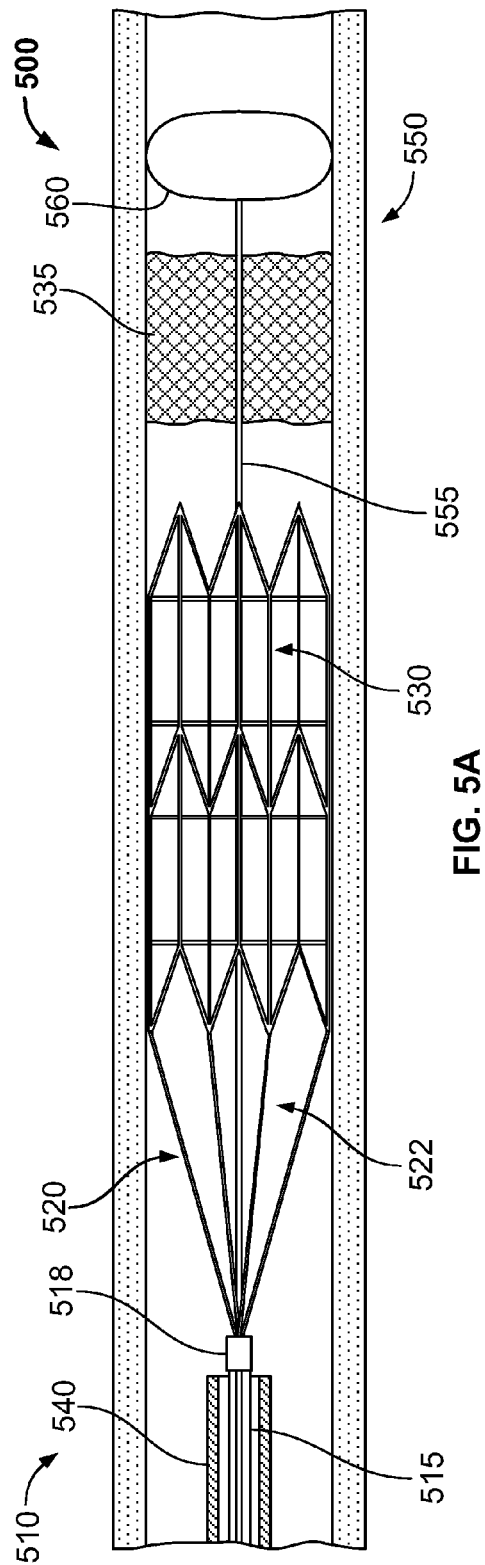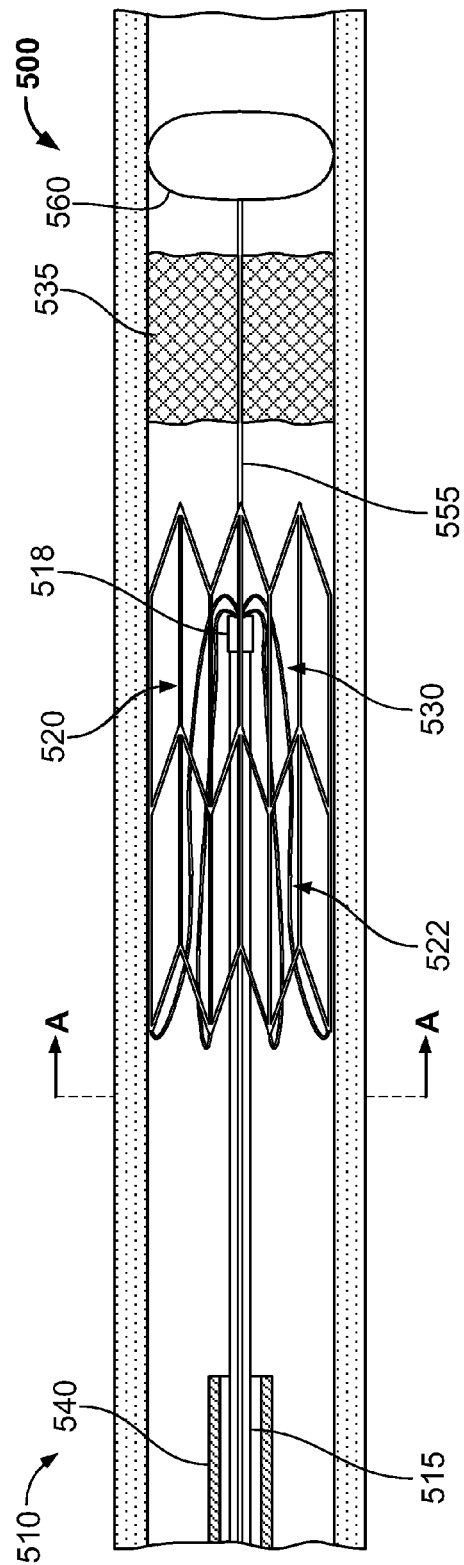
FIG. 5A
FIG. 5B

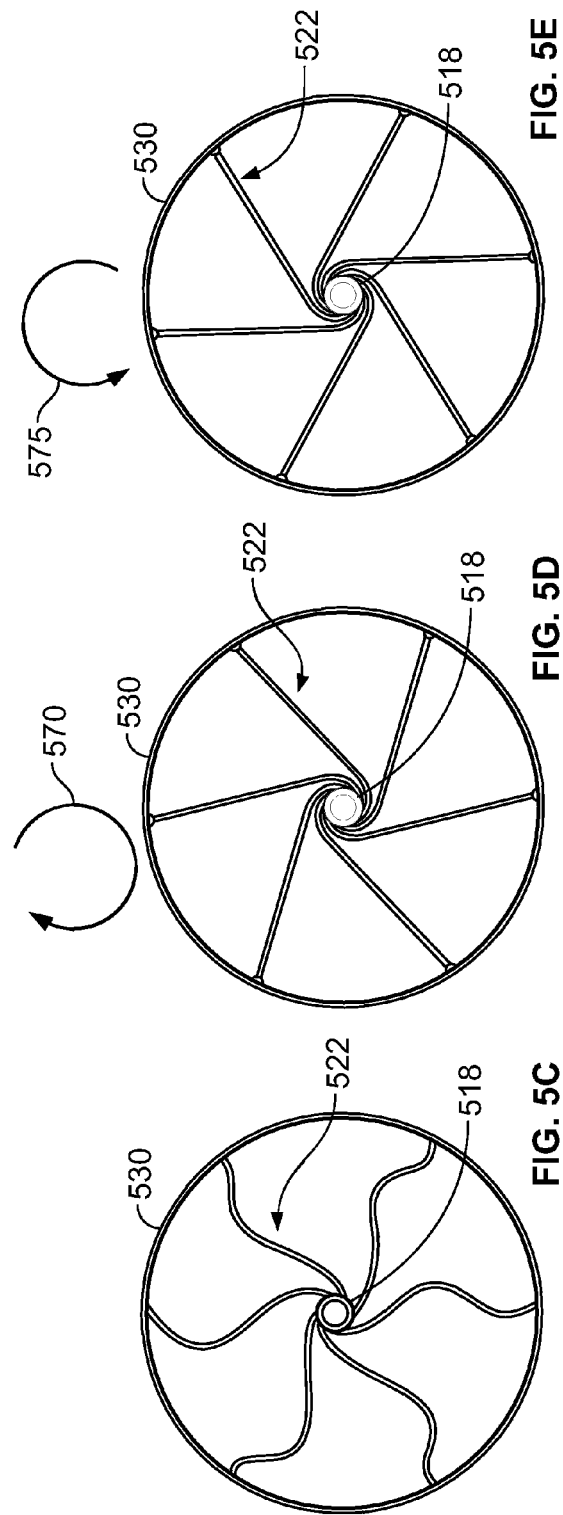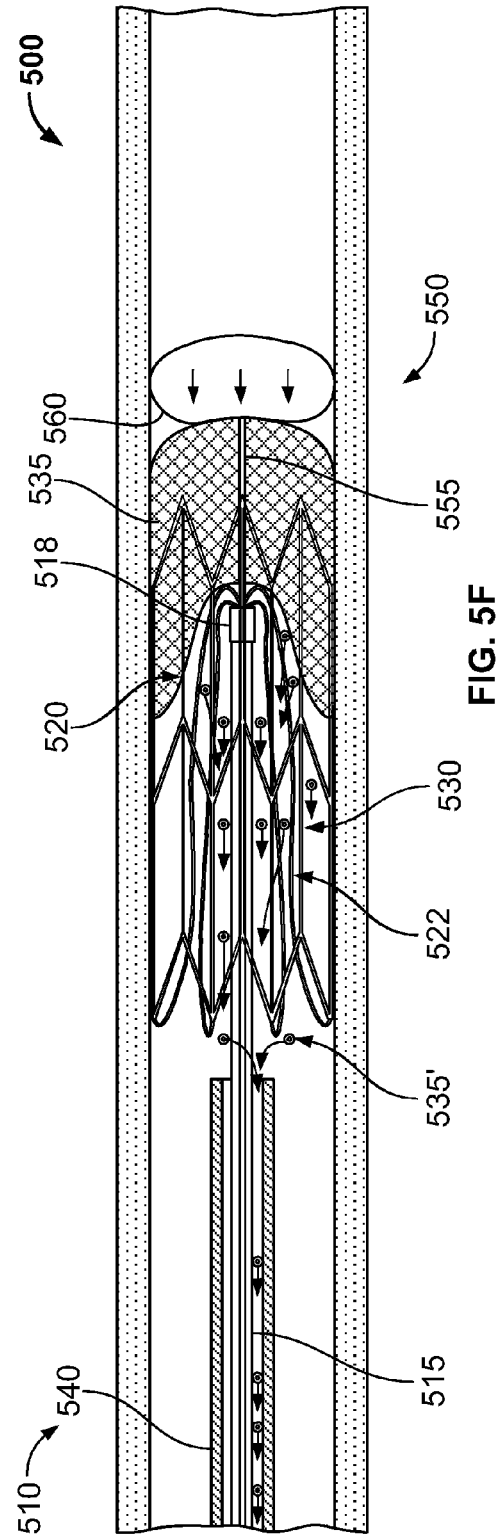

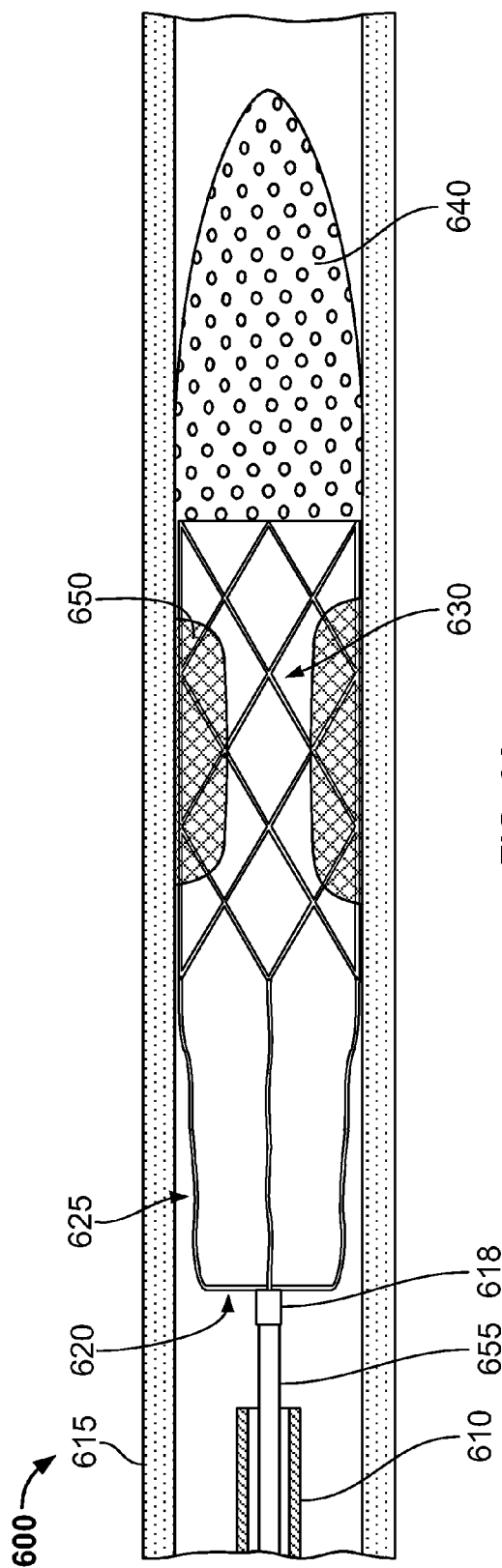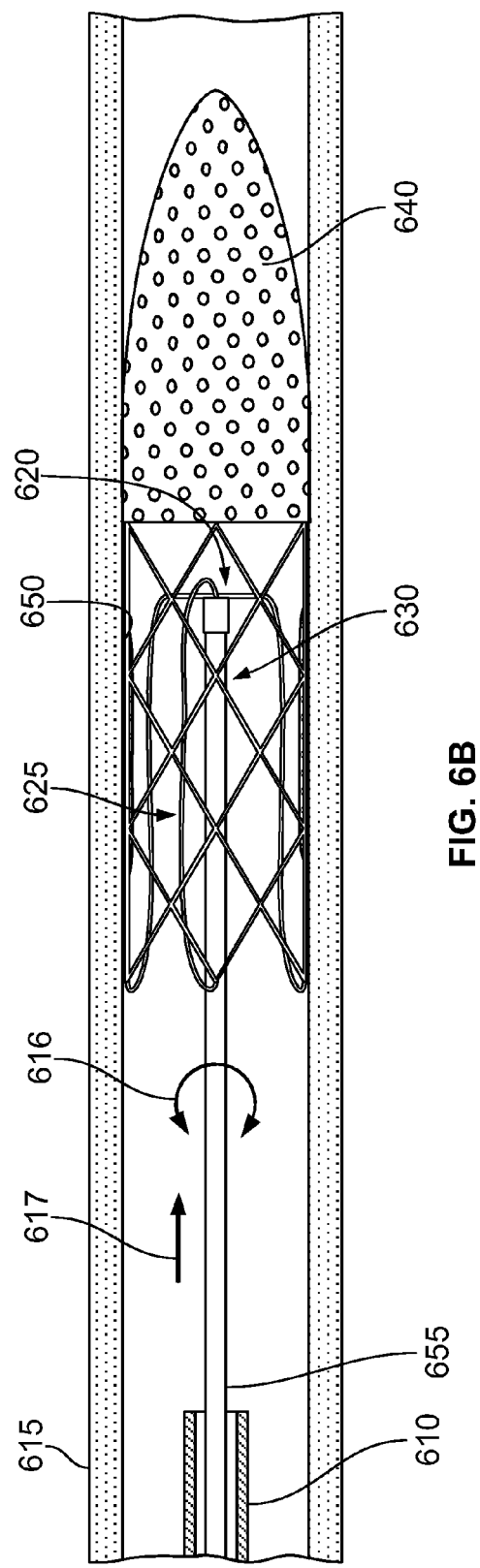
FIG. 6A
FIG. 6B

DEVICES AND SYSTEMS FOR THROMBUS TREATMENT

CROSS-REFERENCE TO RELATED APPLICATIONS

This application claims priority to U.S. Provisional Application No. 61/683,043, filed Aug. 14, 2012. The disclosure of the prior application is considered part of and is incorporated by reference in the disclosure of this application. This application also incorporates by reference the disclosure of the application entitled, "DEVICES AND SYSTEMS FOR THROMBUS TREATMENT", filed on Mar. 13, 2013 Ser. No. 13802437.

TECHNICAL FIELD

This disclosure relates to devices, systems, and methods for treatment of thrombus.

BACKGROUND

Blood clot formation, or "thrombosis," is a basis of a number of serious diseases, such as ischemic stroke, myocardial infarction (heart attack), and deep vein thrombosis (DVT). Blood clots, or "thrombi," form inside blood vessels and obstruct the flow of blood through the circulatory system, thereby depriving tissue and organs of oxygen. In the case of a stroke, for instance, when blood flow to the brain is obstructed for longer than a few seconds, brain cells can die and permanent neurological damage can result.

Thrombi can be treated (reduced or eliminated) by inducing thrombolysis. Thrombolysis is the dissolving, or "lysis," of a thrombus. Thrombolysis can sometimes be induced pharmacologically, such as by administering a tissue plasminogen activator drug (tPA), the most common thrombolytic agent. Thrombolytic agents (commonly called "clot-busting drugs") can be administered via an intravenous line or using a catheter to deliver them proximally to the thrombus. However, thrombolysis by administration of clot-busting drugs has its limitations. For example, to be successful, the clot-busting drugs should be administered within three (3) hours of an acute ischemic stroke, and preferably within two (2) hours. Further, patients who use blood-thinning medications, and certain other medications, are usually not candidates for pharmacological thrombolysis. And of those patients receiving the treatment, it is unsuccessful in dissolving thrombi in approximately 25% of patients.

In view of the limitations of pharmacologically induced thrombolysis, various medical devices for surgically removing thrombi have been developed. The procedure for surgically removing thrombi is generally known as a "thrombectomy." In thrombectomy treatments, a catheter system is typically used to deliver a device to the thrombus. The device can be, for example, an aspiration catheter. Aspiration catheters can perform a thrombectomy by suctioning the thrombus out of the blood vessel. Other thrombectomy procedures use a mechanical device to physically entangle with a thrombus, and to remove the thrombus as the device is removed from the blood vessel. Various types of mechanical devices, such as wires, corkscrew-like coils, bristles, and baskets have been employed to entangle with thrombi.

Some traditional thrombectomy devices can cause damage to blood vessel walls. In addition, some traditional thrombectomy devices can be prone to generating thrombotic fragments that become emboli when they travel within the bloodstream. Emboli can become lodged in arteries, veins, arterioles, and capillaries, and can block the blood supply to vital organs such as the brain or heart. Emboli in the bloodstream can be life-threatening. In the case of DVT treatment, dislodged thromboemboli can travel to the lungs, resulting in a pulmonary embolism, which can be fatal.

SUMMARY

This specification describes devices, systems, and processes for treatment of thrombi. In brief, various embodiments are disclosed for mechanically restoring a blood-flow path, facilitating lysis by blood flow, withdrawing thrombotic material, and capturing thrombotic fragments in a filter device. Additionally, devices, systems, and processes for maceration, aspiration and other adjunct processes are disclosed.

In one general aspect, a thrombus treatment device is provided. The thrombus treatment device includes a support wire; a body frame portion that is disposed about an axis defined by the support wire, wherein a longitudinal length of the body frame portion is at least two times as long as an outer diameter of the body frame portion; a tether portion that includes one or more tethers that extend from the body frame portion to a collar that is coupled to the support wire; and a filter portion that extends from the body frame portion.

In various implementations, the longitudinal length of the body frame portion may be at least three times as long as the outer diameter of the body frame portion. The longitudinal length of the body frame portion may be at least four times as long as the outer diameter of the body frame portion. The longitudinal length of the body frame portion may be at least five times as long as the outer diameter of the body frame portion. A longitudinal length of the filter portion may be less than or equal to one-half of the longitudinal length of the body frame portion. The one or more tethers may be adapted to evert to a configuration wherein the one or more tethers are substantially within an area defined by the body frame portion. The one or more tethers may be comprised of nitinol. The one or more tethers may be comprised of a polymeric material. The device may include multiple tethers that each extend from the body frame portion to the collar that is coupled to the support wire. Each tether of the multiple tethers may be adapted to evert to a configuration wherein each tether of the multiple tethers is substantially within an area defined by the body frame portion. The filter portion may not substantially overlap the body frame portion. The body frame portion may define a plurality of open-faced cells arranged in at least three rows along the longitudinal length of the body frame portion, and the filter portion may overlap the body frame portion by up to one row of the at least three rows and the filter portion may not overlap the remaining body frame portion. The body frame portion may define from three to ten rows of open-faced cells along the longitudinal length of the body frame portion. The filter portion may overlap 20% or less of the longitudinal length of the body frame portion. The one or more tethers may extend from a proximal end of the body frame portion, and the filter portion may extend from a distal end of the body frame portion.

In another general aspect, a method of treating a thrombus is provided. The method comprises: introducing a catheter to a patient and advancing a distal end of the catheter to a treatment site; advancing a thrombus treatment device through a lumen of the catheter; positioning the thrombus treatment device within the lumen of the catheter at a position wherein the body frame portion is generally aligned with at least a portion of a thrombus at the treatment site; and proximally withdrawing the catheter, wherein the body frame portion expands with a radial force sufficient to embed in the thrombus in response to the proximal withdrawal of the catheter. The thrombus treatment device comprises: (a) a body frame portion, (b) a tether portion that includes one or more tethers that extend from the body frame portion to a collar that is coupled to a support wire, and (c) a filter portion that extends from the body frame portion, wherein a longitudinal length of the body frame portion is at least two times as long as an outer diameter of the body frame portion.

In various implementations, the body frame portion may be adapted to open a flow channel through or around the thrombus when the body frame portion expands and contacts the thrombus. The filter portion may be adapted to capture thrombus particles displaced by the expansion of the body frame portion. The method may further comprise pretreating the filter portion with a thrombogenic material or autologous blood. The thrombus treatment device may act as an occluder while the thrombogenic material or autologous blood restricts blood flow through the filter portion. The method may further comprise delivering a thrombolytic agent to the thrombus.

In another general aspect, another thrombus treatment device is provided. The thrombus treatment device comprises: a support tube; a body frame portion that is disposed about an axis defined by the support tube, the body frame portion including a proximal end and a distal end; a filter portion that extends from the distal end of the body frame portion; and multiple tethers each having a first end and a second end, wherein the first end of each of the multiple tethers extends out a proximal end of the support tube, the tethers extending through a lumen of the support tube and out a distal end of the support tube and engaging the body frame portion near the distal end of the body frame portion and extending to the proximal end of the body frame portion, the second end of each of the multiple tethers being attached to the body frame portion near the proximal end of the body frame portion.

In various implementations, each tether of the multiple tethers may form a loop around the body frame portion near the proximal end of the body frame portion. A proximally directed force applied to the first end of each of the multiple tethers may cause the distal end of the body frame portion and the proximal end of the body frame portion to collapse radially toward the axis defined by the support tube. The multiple tethers may collectively form a loop around the body frame portion near the proximal end of the body frame portion. A proximally directed force applied to the first end of each of the multiple tethers may cause the distal end of the body frame portion and the proximal end of the body frame portion to collapse radially toward the longitudinal axis defined by the support tube.

In another general aspect, another method of treating a thrombus is provided. The method comprises: introducing a catheter to a patient and advancing a distal end of the catheter to a treatment site; advancing a thrombus treatment device through a lumen of the catheter; positioning the thrombus treatment device within the lumen of the catheter at a position wherein the body frame portion is generally aligned with at least a portion of a thrombus at the treatment site; and proximally withdrawing the catheter, wherein the body frame portion expands with a radial force sufficient to embed in the thrombus in response to the proximal withdrawal of the catheter. The thrombus treatment device comprises: (a) a support tube, (b) a body frame portion that is disposed about an axis defined by the support tube, the body frame portion including a proximal end and a distal end, (c) a filter portion that extends from the distal end of the body frame portion, and (d) multiple tethers each having a first end and a second end, wherein the first end of each of the multiple tethers extends out a proximal end of the support tube, the tethers extending through a lumen of the support tube and out a distal end of the support tube and engaging the body frame portion near the distal end of the body frame portion and extending to the proximal end of the body frame portion, the second end of each of the multiple tethers being attached to the body frame portion near the proximal end of the body frame portion.

In various implementations, the body frame portion may be adapted to open a flow channel through the thrombus when the body frame portion expands and contacts the thrombus. The filter portion may be adapted to capture thrombus particles displaced by the expansion of the body frame portion. The method may further comprise pretreating the filter portion with a thrombogenic material or autologous blood. The thrombus treatment device may act as an occluder while the thrombogenic material or autologous blood restricts blood flow through the filter portion. The method may further comprise delivering a thrombolytic agent to the thrombus.

In another general aspect, another thrombus treatment device is provided. The thrombus treatment device comprises: a support wire; a body frame portion that is disposed about an axis defined by the support wire, wherein a longitudinal length of the body frame portion is at least two times as long as an outer diameter of the body frame portion; one or more tethers that each extend from a proximal end of the body frame portion to a collar that is coupled to the support wire; and a filter portion that extends from a distal end of the body frame portion. The body frame portion defines a plurality of open-faced cells arranged in at least three rows along the longitudinal length of the body frame portion, and wherein the filter portion overlaps up to one row of the at least three rows and does not overlap the remaining rows.

In various implementations, the longitudinal length of the body frame portion may be at least three times as long as the outer diameter of the body frame portion. The longitudinal length of the body frame portion may be at least four times as long as the outer diameter of the body frame portion. The longitudinal length of the body frame portion may be at least five times as long as the outer diameter of the body frame portion.

In another general aspect, another method of treating a thrombus is provided. The method comprises: inserting a catheter into a patient and advancing a distal end of the catheter to a treatment site; advancing a thrombus treatment device through a lumen of the catheter; positioning the thrombus treatment device within the lumen of the catheter at a position wherein the body frame portion is generally aligned with at least a portion of a thrombus at the treatment site; and proximally withdrawing the catheter, wherein the body frame portion expands with a radial force sufficient to embed in the thrombus in response to the proximal withdrawal of the catheter. The thrombus treatment device comprises: (a) a body frame portion that has a longitudinal length that is at least two times as long as an outer diameter of the body frame portion, (b) a tether portion that includes one or more tethers that each extend from the body frame portion to a collar that is coupled to a support wire, and (c) a filter portion that extends from the body frame portion, wherein the body frame portion defines a plurality of open-faced cells arranged in at least three rows along the longitudinal length of the body frame portion, and wherein the filter portion overlaps up to one row of the at least three rows and does not overlap the remaining rows of the at least three rows.

In various implementations, the body frame portion may be adapted to open a flow channel through the thrombus when the body frame portion expands and contacts the thrombus.

The filter portion may be adapted to capture thrombus particles displaced by the expansion of the body frame portion. The method may further comprise pretreating the filter portion with a thrombogenic material or autologous blood. The thrombus treatment device may act as an occluder while the thrombogenic material or autologous blood restricts blood flow through the filter portion. The method may further comprise delivering a thrombolytic agent to the thrombus.

In another general aspect, another thrombus treatment device is provided. The thrombus treatment device comprises: a support tube; a body frame portion that is disposed about an axis defined by the support tube, the body frame portion including a proximal end and a distal end; a filter portion that extends from the distal end of the body frame portion; one or more proximal tethers each having first and second ends, wherein the first end of each of the one or more proximal tethers is coupled to the support tube, and wherein the second end of each of the one or more proximal tethers is coupled to the body frame portion; and one or more distal tethers each having first and second ends, wherein the first end of each of the one or more distal tethers is coupled to the support tube, and wherein the second end of each of the one or more distal tethers is coupled to the body frame portion.

In various implementations, the one or more distal tethers may be movably coupled to the support tube, and wherein the one or more proximal tethers may be fixedly coupled to the support tube. The one or more distal tethers may be fixedly coupled to the support tube, and the one or more proximal tethers may be movably coupled to the support tube. A distal end of the support tube may be located distally of a location where the distal tethers are coupled to the support tube. A distal end of the support tube may be located distally of the filter portion. The distal tethers may be located substantially within an interior space defined by the filter portion. A longitudinal length of the body frame portion may be at least two times as long as an outer diameter of the body frame portion. A longitudinal length of the body frame portion may be at least three times as long as an outer diameter of the body frame portion. A longitudinal length of the body frame portion may be at least four times as long as an outer diameter of the body frame portion. A longitudinal length of the filter portion may be less than or equal to one-half of a longitudinal length of the body frame portion. The second end of each of the one or more proximal tethers may be coupled to the proximal end of the body frame portion, and the second end of each of the one or more distal tethers may be coupled to the distal end of the body frame portion.

In another general aspect, another method for treating a thrombus is provided. The method comprises: inserting a catheter into a patient and advancing a distal end of the catheter to a treatment site; advancing a thrombus treatment device through a lumen of the catheter; positioning the thrombus treatment device within the lumen of the catheter at a position wherein the body frame portion is generally aligned with at least a portion of a thrombus at the treatment site; and proximally withdrawing the catheter, wherein the body frame portion expands with a radial force sufficient to embed in the thrombus in response to the proximal withdrawal of the catheter. The thrombus treatment device comprises: a support tube; a body frame portion that is disposed about an axis defined by the support tube, the body frame portion including a proximal end and a distal end; a filter portion that extends from the distal end of the body frame portion; one or more proximal tethers each having first and second ends, wherein the first end of each of the one or more proximal tethers is coupled to the support tube, and wherein the second end of each of the one or more proximal tethers is coupled to the body frame portion; and one or more distal tethers each having first and second ends, wherein the first end of each of the one or more distal tethers is coupled to the support tube, and wherein the second end of each of the one or more distal tethers is coupled to the body frame portion.

In various implementations, the body frame portion may be adapted to open a flow channel through the thrombus when the body frame portion expands and contacts the thrombus. The filter portion may be adapted to capture thrombus particles displaced by the expansion of the body frame portion.

In another general aspect, another thrombus treatment device is provided. The thrombus treatment device comprises: a support wire; a body frame portion that is disposed about an axis defined by the support wire, wherein the body frame portion defines one or more interstices; a tether portion that includes one or more tethers, said one or more tethers extending from the body frame portion to a collar that is coupled to the support wire; and a filter portion that extends from the body frame portion, wherein, when the collar is positioned substantially within a region interior of the body frame portion or filter portion, articulation of the support wire causes a portion of the one or more tethers to move through a range of motion and does not impart substantial motion to the body frame portion.

In various implementations, the articulation of the support may be a rotation of said support wire and may cause substantially zero motion of the body frame portion. The device may include, with respect to the rotation of the support wire, a neutral position associated with a zero-degree rotation of the support wire, a first torqued position associated with a clockwise rotation of the support wire, and a second torqued position associated with a counter-clockwise rotation of the support wire. The one or more tethers may comprise an "S" shape when the device is in the neutral position. The one or more tethers may comprise a first generally linear shape when the device is in the first torqued position, and may comprise a second generally linear shape when the device is in the second torqued position. The one or more tethers may comprise a looped configuration when the device is in the neutral position. The one or more tethers may be adapted to sever, when the support wire is articulated, at least a portion of thrombotic material that protrudes through the one or more interstices defined by the body frame portion. The articulation of the support wire may be a rotation of the support wire up to 270 degrees and may cause the portion of the one or more tethers to sweep through a range of motion and may not impart substantial motion to the body frame portion. The articulation of the support wire may be a rotation of the support wire up to 180 degrees and may cause the portion of the one or more tethers to sweep through a range of motion and may not impart substantial motion to the body frame portion. The articularion of the support may be a rotation of said support wire up to 360 degrees and may cause substantially zero motion of the body frame portion.

In another general aspect, another method of treating a thrombus is provided. The method comprises: inserting a catheter having a proximal end and a distal end into a patient and advancing the distal end of the catheter to a treatment site; advancing a thrombus treatment device to the treatment site through a lumen of the catheter; positioning the thrombus treatment device within the lumen of the catheter at a position wherein the body frame portion is generally aligned with at least a portion of a thrombus at the treatment site, and proximally withdrawing the catheter; providing a distally directed force to the support wire to advance the collar to a location substantially within a region interior of the body frame portion or substantially within a region interior of the filter portion; and rotationally actuating the support wire, wherein the rotational actuation of the support wire causes a swiveling motion of at least a portion of the one or more tethers, the one or more tethers being adapted to macerate the thrombus. The thrombus treatment device comprises: (a) a body frame portion, wherein the body frame portion defines one or more interstices, (b) a tether portion that includes one or more tethers, said one or more tethers extending from the body frame portion to a collar that is coupled to a support wire, and (c) a filter portion that extends from the body frame portion.

In various implementations, the swiveling motion of the portion of the one or more tethers may sever thrombotic material that protrudes through one or more interstices defined by the body frame portion. A rotation of the support wire may cause the portion of the one or more tethers to sweep through a range of motion without imparting substantial motion to the body frame portion. The rotation of the support wire through about 360 degrees may cause substantially zero motion at the body frame portion. A rotation of the support wire through about 270 degrees may cause the portion of the one or more tethers to sweep through a range of motion without imparting substantial motion to the body frame portion. The rotation of the support wire up to at least about 270 degrees may cause substantially zero motion at the body frame portion. A rotation of the support wire through about 180 degrees may cause the portion of the one or more tethers to sweep through a range of motion without imparting substantial motion to the body frame portion. The rotation of the support wire may cause substantially zero motion at the body frame portion. The device may include, with respect to the rotational actuation, a neutral position associated with a zero-degree rotation of the support wire, a first torqued position associated with a clockwise rotation of the support wire, and a second torqued position associated with a counter-clockwise rotation of the support wire. The one or more tethers may comprise an "S" shape when the device is in the neutral position. The one or more tethers may comprise a first generally linear shape when the device is in the first torqued position, and may comprise a second generally linear shape when the device is in the second torqued position. The one or more tethers may comprise a looped configuration when the device is in the neutral position. When the support wire is rotated, the one or more tethers may be adapted to sever thrombotic material that protrudes through the one or more interstices defined by the body frame portion.

In another general aspect, a thrombus treatment system is provided. The thrombus treatment system comprises: a first support tube; a body frame portion that is disposed about an axis defined by the first support tube, wherein the body frame portion defines one or more interstices; a tether portion that includes one or more tethers, said one or more tethers extending from the body frame portion to a collar that is coupled to the first support tube; and a stabilization element attached to a second support tube, wherein, when the collar is positioned substantially within a region interior of the body frame portion, a rotation of the first support tube up to 360 degrees causes a portion of the one or more tethers to sweep through a range of motion and does not impart substantial motion to the body frame portion.

In various implementations, the one or more tethers may extend from a proximal end of the body frame portion. The one or more tethers may extend from a distal end of the body frame portion. The one or more tethers may be adapted to sever thrombotic material that enters a region defined by the body frame portion in response to a proximally directed force applied to the second support tube. A rotation of the first support tube up to 270 degrees may cause the portion of the one or more tethers to sweep through a range of motion and may not impart substantial motion to the body frame portion. A rotation of the first support tube up to 180 degrees may cause the portion of the one or more tethers to sweep through a range of motion and may not impart substantial motion to the body frame portion.

In another general aspect, another method of treating a thrombus is provided. The method comprises: inserting a catheter into a patient and advancing a distal end of the catheter to a treatment site; advancing a thrombus treatment device to the treatment site through a lumen of the catheter; advancing the second support tube to a location where the stabilization element is distal of at least a portion of a thrombus at the treatment site; positioning the body frame portion within the lumen of the catheter at a position proximal of at least a portion of the thrombus; proximally withdrawing the catheter, whereby the body frame portion expands; providing a distally directed force to the first support tube to advance the collar to a location interior of the body frame portion; providing a proximally directed force to the second support tube thereby causing the stabilization element to move proximally; and rotationally actuating the first support tube, wherein the rotational actuation of the first support tube causes a swiveling motion of at least a portion of the one or more tethers, and wherein the one or more tethers are adapted to macerate the thrombus. The thrombus treatment device comprises: (a) a first support tube, (b) a body frame portion that is disposed about an axis defined by the first support tube, (c) a tether portion that includes one or more tethers, said one or more tethers extending from the body frame portion to a collar that is coupled to the first support tube, wherein, when the collar is positioned substantially within a region interior of the body frame portion, a rotation of the first support tube up to 360 degrees causes a portion of the one or more tethers to sweep through a range of motion and does not impart substantial motion to the body frame portion, and (d) a stabilization element attached to a second support tube.

In various implementations, the swiveling motion of the at least a portion of the one or more tethers may macerate thrombotic material that is displaced proximally by the proximal movement of the stabilization element. The device may include, with respect to the rotational actuation, a neutral position associated with a zero-degree rotation of the first support tube, a first torqued position associated with a clockwise rotation of the first support tube, and a second torqued position associated with a counter-clockwise rotation of the first support tube. The one or more tethers may comprise an "S" shape when the device is in the neutral position. The one or more tethers may comprise a first generally linear shape when the device is in the first torqued position, and may comprise a second generally linear shape when the device is in the second torqued position. The one or more tethers may comprise a looped configuration when the device is in the neutral position. The method may further comprise, after advancing the second support tube to a location where the stabilization element is distal of at least a portion of a thrombus at the treatment site, supplying an inflation medium to the stabilization element to cause the stabilization element to expand. The inflation medium may be one of a liquid, a gas, a gel, a foam, and a solid. The inflation medium may include a contrast agent.

In another general aspect, another thrombus treatment system is provided. The thrombus treatment system comprises: a first support tube; a body frame portion that is circumferentially disposed about an axis defined by the first support tube; a first tether portion that includes one or more first tethers, said one or more first tethers extending from a proximal portion of the body frame portion to a first collar that is coupled to the first support tube; a second tether portion that includes one or more second tethers, said one or more second tethers extending from a distal portion of the body frame portion to a second collar that is coupled to the first support tube; and a stabilization element attached to a second support tube, wherein, when the first collar and the second collar are each positioned within a region interior of the body frame portion, a rotation of the first support tube causes portions of the one or more first tethers and the one or more second tethers to sweep through a range of motion and does not impart substantial motion to the body frame portion.

In various implementations, a rotation of the first support tube up to 360 degrees may cause portions of the one or more first tethers and the one or more second tethers to sweep through a range of motion and may not impart substantial motion to the body frame portion. A rotation of the first support tube up to 180 degrees may cause portions of the one or more first tethers and the one or more second tethers to sweep through a range of motion and may not impart substantial motion to the body frame portion.

In another general aspect, another method of treating a thrombus is provided. The method comprises: inserting a catheter into a patient and advancing a distal end of the catheter to a treatment site; advancing a thrombus treatment device to the treatment site through a lumen of the catheter; advancing the second support tube to a location where the stabilization element is distal of at least a portion of a thrombus at the treatment site; positioning the body frame portion within the lumen of the catheter at a position proximal of at least a portion of the thrombus; proximally withdrawing the catheter, whereby the body frame portion expands; positioning the first and second collars within the region interior of the body frame portion; providing a proximally directed force to the second support tube thereby causing the stabilization element to move proximally; and rotationally actuating the first support tube, wherein the rotational actuation of the first support tube causes a swiveling motion of a portion of the one or more first tethers and of a portion of the one or more second tethers, and wherein the one or more first tethers and the one or more second tethers are adapted to macerate the thrombus. The thrombus treatment device comprises: (a) a first support tube, (b) a body frame portion that is circumferentially disposed about an axis defined by the first support tube, (c) a first tether portion that includes one or more first tethers, said one or more first tethers extending from a proximal portion of the body frame portion to a first collar that is coupled to the first support tube, (d) a second tether portion that includes one or more second tethers, said one or more second tethers extending from a distal portion of the body frame portion to a second collar that is coupled to the first support tube, wherein, when the first collar and the second collar are each positioned within a region interior of the body frame portion, a rotation of the first support tube up to 360 degrees causes portions of the one or more first tethers and the one or more second tethers to sweep through a range of motion and does not impart substantial motion to the body frame portion, and (e) a stabilization element attached to a second support tube.

In various implementations, the swiveling motion of the portion of the at least one first tethers and of the portion of the at least one second tethers may macerate thrombotic material that is displaced proximally by the proximal movement of the stabilization element. The device may include, with respect to the rotational actuation, a neutral position associated with a zero-degree rotation of the first support tube, a first torqued position associated with a clockwise rotation of the first support tube, and a second torqued position associated with a counter-clockwise rotation of the first support tube. The one or more first tethers may comprise an "S" shape when the device is in the neutral position, and the one or more second tethers may comprise the "S" shape when the device is in the neutral position. The one or more first tethers and the one or more second tethers may comprise first generally linear shapes when the device is in the first torqued position, and may comprise second generally linear shapes when the device is in the second torqued position. The one or more first tethers and the one or more second tethers may comprise looped configurations when the device is in the neutral position. The method may further comprise, after advancing the second support tube to a location where the stabilization element is distal of at least a portion of a thrombus at the treatment site, supplying an inflation medium to the stabilization element to cause the stabilization element to expand. The inflation medium may be one of a liquid, a gas, a gel, a foam, and a solid. The inflation medium may include a contrast agent.

In another general aspect, another thrombus treatment system is provided. The thrombus treatment system comprises: a first support tube and a second support tube; a body frame portion; a first tether portion that includes one or more first tethers, said one or more first tethers extending from a proximal portion of the body frame portion to a first collar that is coupled to the first support tube; a second tether portion that includes one or more second tethers, said one or more second tethers extending from a distal portion of the body frame portion to a second collar that is coupled to the second support tube; and a stabilization element attached to a third support tube, wherein, when the first collar and the second collar are each positioned substantially within a region interior of the body frame portion, a rotational actuation of the first support tube causes a swiveling motion of a portion of the one or more first tethers, and rotational actuation of the second support tube causes a swiveling motion of a portion of the one or more second tethers.

In various implementations, the first tube and the second tube may be adapted to be counter-rotated to cause a first swiveling motion of the one or more first tethers and a second swiveling motion of the one or more second tethers.

In another general aspect, another method of treating a thrombus is provided. The method comprises: inserting a catheter into a patient and advancing a distal end of the catheter to a treatment site; advancing a thrombus treatment device to the treatment site through a lumen of the catheter; advancing the third support tube to a location where the stabilization element is distal of at least a portion of a thrombus at the treatment site; positioning the body frame portion within the lumen of the catheter at a position proximal of at least a portion of the thrombus; proximally withdrawing the catheter, whereby the body frame portion expands; positioning the first and second collars substantially within the region interior of the body frame portion; providing a proximally directed force to the third support tube thereby causing the stabilization element to move proximally; and rotationally actuating the first and second support tubes, wherein the rotational actuation of the first support tube causes a swiveling motion of a portion of the one or more first tethers and the rotational actuation of the second support tube causes a swiveling motion of a portion of the one or more second tethers, and wherein the one or more first tethers and the one or more second tethers are adapted to macerate the thrombus. The thrombus treatment device comprises: (a) a first support tube, (b) a second support tube, (c) a body frame portion, (d) a first tether portion that includes at one or more first tethers, said one or more first tethers extending from a proximal portion of the body frame portion to a first collar that is coupled to the first support tube, (e) a second tether portion that includes one or more second tethers, said one or more second tethers extending from a distal portion of the body frame portion to a second collar that is coupled to the second support tube, and (f) a stabilization element attached to a third support tube.

In various implementations, the first tube and the second tube may be counter-rotated to cause a first swiveling motion of the one or more first tethers and a second swiveling motion of the one or more second tethers. The swiveling motion of the portion of the one or more first tethers and of the portion of the one or more second tethers may macerate thrombotic material that is displaced proximally by the proximal movement of the stabilization element. The device may include, with respect to the rotational actuation, a neutral position associated with a zero-degree rotation of the first and second support tubes, a first torqued position associated with a clockwise rotation of the first and second support tubes, and a second torqued position associated with a counter-clockwise rotation of the first and second support tubes. The one or more first tethers may comprise an "S" shape when the device is in the neutral position, and the one or more second tethers may comprise the "S" shape when the device is in the neutral position. The one or more first tethers and the one or more second tethers may comprise first generally linear shapes when the device is in the first torqued position, and may comprise second generally linear shapes when the device is in the second torqued position. The one or more first tethers and the one or more second tethers may comprise looped configurations when the device is in the neutral position. The method may further comprise, after advancing the third support tube to a location where the stabilization element is distal of at least a portion of a thrombus at the treatment site, supplying an inflation medium to the stabilization element to cause the stabilization element to expand. The inflation medium may be one of a liquid, a gas, a gel, a foam, and a solid. The inflation medium may include a contrast agent.

In another general aspect, another method of treating a thrombus is provided. The method comprises: inserting a catheter into a patient and advancing a distal end of the catheter to a treatment site; advancing a thrombus treatment device to the treatment site through a lumen of the catheter; positioning the thrombus treatment device within the lumen of the catheter at a position wherein the body frame portion is generally aligned with at least a portion of a thrombus at the treatment site, and proximally withdrawing the catheter; providing a distally directed force to the support wire to advance the collar to a location substantially within an interior of the body frame portion; and providing a proximally directed force to the support wire to withdraw the collar to a location exterior of the body frame portion, wherein the advancing and withdrawing of the collar causes a motion of at least a portion of the one or more tethers, the one or more tethers being adapted to macerate the thrombus. The thrombus treatment device comprises: (a) a body frame portion, (b) a tether portion that includes one or more tethers, said one or more tethers extending from the body frame portion to a collar that is coupled to a support wire, and (c) a filter portion that extends from the body frame portion.

In another general aspect, another thrombus treatment device is provided. The thrombus treatment device comprises: a support wire; a body frame portion that is disposed about an axis defined by the support wire, wherein the body frame portion defines one or more interstices; a tether portion that includes one or more tethers, said one or more tethers extending from the body frame portion to a collar that is coupled to the support wire; and a filter portion that extends from the body frame portion, wherein, when the collar is positioned substantially within a region interior of the body frame portion or filter portion, a manipulation of the support wire causes a portion of the one or more tethers to move through a range of motion and does not impart substantial motion to the body frame portion.

In various implementations, the manipulation of the support wire may be a linear movement substantially parallel to the axis. The manipulation of the support wire may be a rotational movement. The rotational movement of the support wire may be up to 360 degrees. The rotational movement of the support wire may be up to 270 degrees. The rotational movement of the support wire may be up to 180 degrees. The device may include, with respect to the rotation of the support wire, a neutral position associated with a zero-degree rotation of the support wire, a first torqued position associated with a clockwise rotation of the support wire, and a second torqued position associated with a counter-clockwise rotation of the support wire. The one or more tethers may comprise an "S" shape when the device is in the neutral position. The one or more tethers may comprise a first generally linear shape when the device is in the first torqued position, and may comprise a second generally linear shape when the device is in the second torqued position. The one or more tethers may comprise a looped configuration when the device is in the neutral position. The one or more tethers may be adapted to sever, when the support wire is rotated, at least a portion of thrombotic material that protrudes through the one or more interstices defined by the body frame portion.

Particular embodiments of the subject matter described in this specification can be implemented so as to realize one or more of the following advantages. Treatment to reduce thrombi and restore blood flow can be administered while preventing the release of thromboemboli into the bloodstream. Thrombotic material can be macerated and removed while protecting blood vessel walls from potential trauma. A single device can provide a treatment platform for performing multiple procedures, such as thrombolysis, aspiration, maceration, and thrombectomy, while providing thromboembolic protection.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 1 illustrates an example thrombectomy device.

FIGS. 2A-2I are a series of illustrations depicting an example manner of use of an example thrombectomy device.

FIGS. 5A-5F illustrate an example thrombectomy system and an example manner of use of an example thrombectomy system.

FIGS. 6A-6B illustrate an example thrombectomy system and an example manner of use of an example thrombectomy system.

Like reference numbers and designations in the various drawings indicate like elements.

DETAILED DESCRIPTION

Figure 2A:
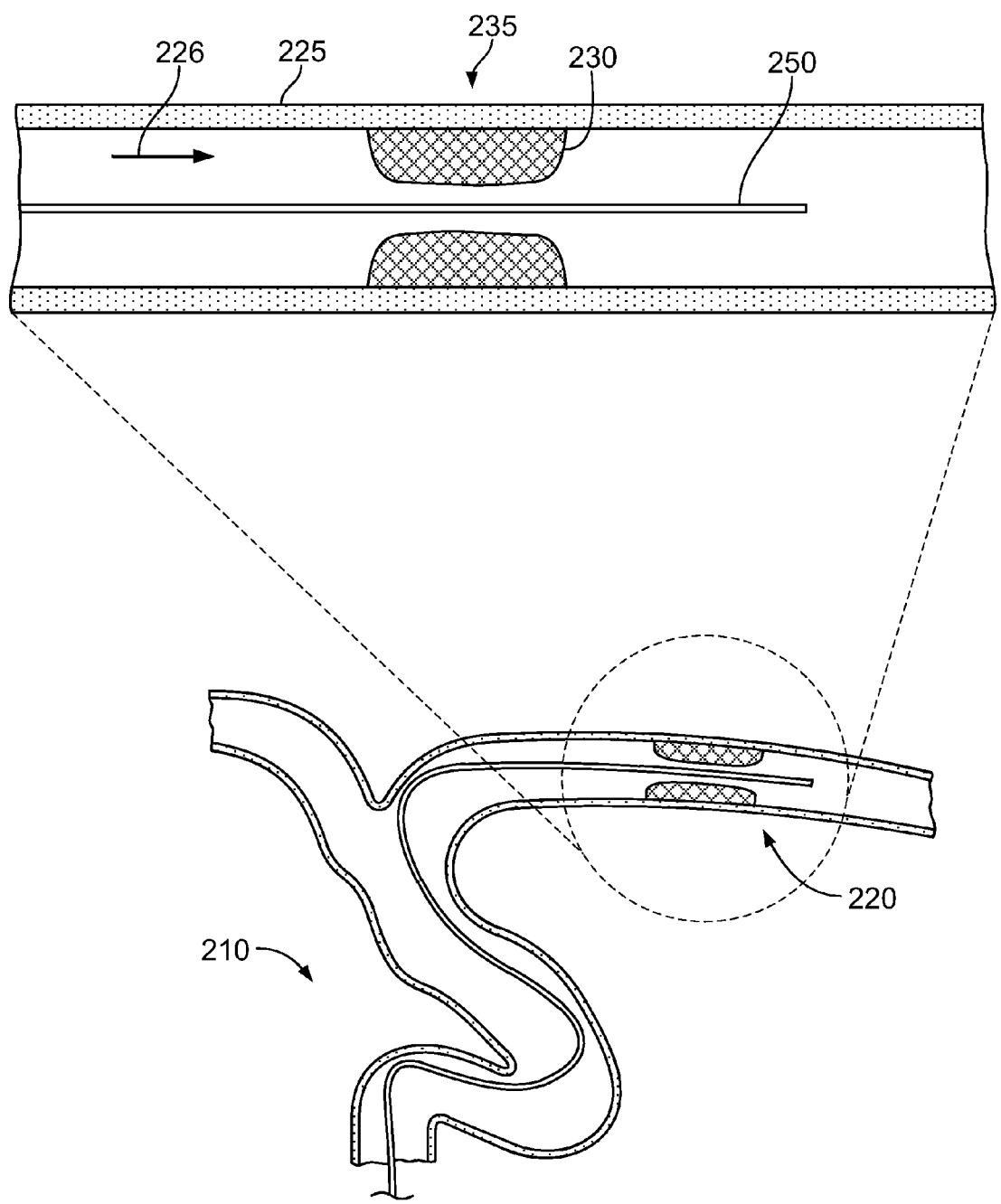

FIG. 1 illustrates an example embodiment of a thrombectomy device 10. This device can be delivered percutaneously and through a patient's vasculature to the site of a thrombus, such as a neurovascular, cardiovascular, or peripheral vein thrombus site. The thrombectomy device 10 may be used in both antegrade and retrograde applications.

The example thrombectomy device 10 generally includes a support wire 15 and a distal device body 12 including three (3) primary components: (i) a tether assembly 20, (ii) a body frame 30, and (iii) a filter bag 40. A central collar 18 can couple the tether assembly 20 to the support wire 15. The distal device body is collapsible so it can be contained within a catheter lumen for delivery through the patient's vasculature to the location of a thrombus (refer, e.g., to FIGS. 2D and 2E). At the thrombus site, the thrombectomy device 10 can be deployed outwardly from the distal tip of the delivery catheter, at which time the thrombectomy device 10 can expand to the unconstrained configuration shown in FIG. 1.

The support wire 15 can include a solid or hollow support wire, or can include any other tubular article with at least one continuous lumen running therethrough. A suitable support wire 15 for use with the thrombectomy device 10 may include, but is not limited to, a guide wire or a tube (e.g., a support tube). In general, the support wire 15 can enable the thrombectomy device 10 to be delivered through tortuous vascular anatomies and positioned in distal vascular areas. In some embodiments, support wire 15 extends through the distal end of the filter bag 40 to become the most distal component of the thrombectomy device 10. In some embodiments, support wire 15 extends into the distal device body 12 but not through the distal end of the filter bag 40. In some embodiments, a support wire 15 that extends distally from at least the body frame 30 can also include one or more balloon devices disposed near the distal end.

In some embodiments, the support wire 15 is a flexible driveshaft as described in the patent application titled "Flexible Driveshafts with Bi-Directionally Balanced Torsional Stiffness Properties," having inventor Clifford P. Warner, filed on the same date as this application, and which is herein incorporated by reference in its entirety for all purposes.

The tether assembly 20 of the thrombectomy device 10 includes one or more tethers 22. The tethers 22 are generally elongate elements that can be coupled on one end with the support wire 15 (using one or more collars, such as central collar 18), and the tethers 22 can be coupled with the body frame 30 at the tether's 22 opposite end. In some embodiments, the tethers 22 extend from the support wire 15 to the proximal end of the body frame 30 (as shown). In some embodiments, the tethers 22 extend from the support wire 15 to the distal end of the body frame 30 (not shown). In some embodiments, the tethers 22 extend from the support wire 15 to locations on the body frame 30 between the proximal and distal ends of the body frame 30 (not shown). While in some embodiments just one tether 22 is included, some embodiments include two, three, four, or more tethers 22.

The length of the tethers 22 can be determined in accordance with the operational characteristics desired. For example, in some applications a short deployment length is desired, leading to a selection of short or looped support strut tethers 20. In some applications the ability to evert the tethers 22 within the body frame 30 or filter bag 40 leads to a selection of using longer tethers 22, which may also be looped in some examples. For example, in some embodiments the tethers 22 can be at least as long as the combined length of the body frame 30 and filter bag 40. In some implementations, the tethers can be at least twice as long as a diameter defined by the frame body 30 in an unconstrained configuration.

In some embodiments, the tethers 22 of a thrombectomy device 10 are of substantially equal length. In some embodiments, one or more tethers 22 are unequal in length in comparison to one or more other tethers 22. In some embodiments, the tethers 22 of a thrombectomy device 10 are of substantially equal cross-sectional size and/or shape. In some embodiments, one or more tethers 22 are unequal in cross-sectional size and/or shape in comparison to one or more other tethers 22.

The tethers 22 can be comprised of generally flexible biocompatible materials. For example, in some embodiments the tethers 22 can be made from nitinol that exhibits superelasticity. In some embodiments, the tethers 22 may be made from the same material as the body frame 30. In other embodiments, the tethers 22 can be a polymeric material that is highly flexible. In some embodiments the tethers 22 can be made from a combination of biocompatible materials that, when combined, exhibit appropriate flexibility. In some examples, the tethers 22 can include a nitinol component and a polymeric material component. In some embodiments, the tethers 22 have mechanical properties that make them suitable for performing maceration of thrombus material as described further below (refer to FIGS. 2G, 5F, and 6B). For example, in some such embodiments the tethers 22 have a stiffness and sharpness that can facilitate their effectiveness as maceration implements.

The tethers 22 can be configured as "looped support struts" as described in U.S. Pat. No. 8,231,650 to Cully et al., which is hereby incorporated by reference in its entirety for all purposes. When the tethers 22 are configured in the looped support strut embodiment, the tethers 22 may be essentially s-shaped in some embodiments, and the central collar 18 can be everted within the interior of the body frame 30 or the filter bag 40, as will be described below (e.g., in regard to FIG. 2G).

The tethers 22 can serve multiple purposes. For example, one purpose of the tethers 22 can be to couple the distal device body 12 of the thrombectomy device 10 to the support wire 15. Another purpose of the tethers 22 can be to enable flexible compliance between the body frame 30 and the contours of irregularly shaped thrombi or vessel walls. Another purpose can be to provide supplemental radial force between the body frame 30 and a thrombus so as to open (also known as recanalization) or maintain a blood-flow path. Another purpose (as described further below) can be to sever, shave, or break up thrombi by everting and causing a pivoting motion of the tethers 22 as a part of a thrombectomy procedure. In some implementations, the tethers 22 need not be everted to sever, shave, or break up thrombi and participate in the thrombectomy procedure. In some implementations, the tethers 22 may be coated with an abrasive material, which may aid the tethers in severing, shaving, or breaking up thrombi when pivotal motion is applied to the tethers 22. In some implementations, a portion of the tethers may be sharpened, which may aid the tethers in severing, shaving, or breaking up thrombi when pivotal motion is applied to the tethers 22.

The body frame 30 can be metallic, for example, constructed of nitinol, stainless steel, titanium, or a combination of materials. The body frame 30 materials can, in some embodiments, be laser cut to the desired configuration. In some embodiments body frame 30 can have a polymeric covering or powder coating over a metallic frame. In general, the body frame 30 can be collapsible to fit within the lumen of a delivery catheter. The body frame 30 can radially self-expand to an unconstrained configuration when deployed from the catheter. The unconstrained body frame 30 can be circular in cross-section, or another cross-sectional shape such as a partial circle or an oval. In some embodiments, the body frame 30 can have a tapered profile. In some implementations, the body frame 30 will radially self-expand to conform to the cross-sectional shape of a vessel in which the body frame 30 is deployed.

The length of the body frame 30 can be determined in accordance with the operational characteristics desired, such as the length, thickness, shape, and the location of the thrombus to be treated. The body frame 30 can be made longer by, for example, by adding more rows of struts or support members to the body frame 30, or by increasing the length of one or more existing rows of struts. The terms "row" or "rows" as used in relation to the body frames of the devices provided herein refers to a peripheral portion of the body frame (e.g., a complete helical turn around the circumference, circumferential ring, or cylindrical portion) corresponding to a segment of the framework of the device. The body frame 30 can be constructed using any suitable configuration of struts or support members. For example, in some embodiments the body frame 30 is a helical structure comprising helical rows of strut members. In some embodiments, the body frame 30 is an assembly of one or more circumferential rings (or rows) of strut members.

In some embodiments, the ratio of the length of the body frame 30 to the outer diameter of the body frame 30 when the thrombectomy device 10 is in an unconstrained and expanded state is about 1:1, about 2:1, about 3:1, about 4:1, about 5:1, about 6:1, about 7:1, about 8:1, or more than about 8:1. As described further below, the body frame 30 can be positioned in alignment with a target thrombus and can be deployed to expand within and/or around the thrombus to open or enlarge a blood-flow path through and/or around the thrombus. In other words, to recanalize the blood-flow path.

The diameter of the body frame 30 can be generally correlated to the size of the vessel in which the thrombectomy device 10 will be deployed. For example, in some applications, some embodiments have a body frame 30 diameter of about 2 mm to about 6 mm, or about 4 mm to about 8 mm, or larger. In other applications, some embodiments have a body frame 30 diameter of about 8 mm to about 12 mm, about 10 mm to about 16 mm, about 14 mm to about 22 mm, about 20 mm to about 28 mm, or larger. As illustrated by these two examples, a continuum of body frame 30 diameter sizes are envisioned within the scope of this document. That is, a thrombectomy device 10 can be appropriately sized to treat any and all bodily vessels. In some embodiments, devices with a generally smaller size are used in neurovascular applications. In some embodiments, devices with a generally larger size are used in peripheral vein applications.

In some embodiments, the body frame 30 can have a generally open lattice construction. That is, in the expanded configuration, the wall of the body frame 30 can have a substantial amount of area that is open (areas that are not blocked by frame material). In some embodiments, the wall of the body frame 30 can have a higher density of frame material (such as strut elements 32). In comparison, open lattice construction may allow for more penetration of thrombus material while providing less radial displacement of thrombus material, whereas a higher density of frame material may allow for more radial displacement (compaction) of thrombus material and less penetration of thrombus material. Thus, a body frame 30 with a generally open lattice construction can, in some embodiments, be well-suited to allowing penetration of thrombus material within the interior of the body frame 30 where the thrombus material can be detached and removed (reference FIGS. 2G, 2H, and 6B); and a body frame 30 with higher density of frame material can, in some embodiments, be well-suited to compressing thrombus material against the wall of a vessel, thereby facilitating recanalization of the vessel. In some embodiments, the body frame 30 can be designed to provide an appropriate blend of both thrombus penetration and radial displacement of thrombus, or predominantly one or the other, as desired.

Strut elements 32, in some embodiments, can be connected by bridge elements. The strut elements 32 can include a variety of configurations, such as diamond-shaped, "v"-shaped, and braided mesh. In some embodiments where the strut elements 32 form generally diamond-shaped cells (see, e.g., FIG. 3), the device may be lengthened by adding another row of diamond cells. To enhance the compliance of the body frame 30 with irregularly-shaped vessel configurations, in some embodiments, highly-flexible interstitial linkage members can be included to interconnect adjacent rows of strut elements 32. The linkage members can be, in some embodiments, comprised of expanded polytetrafluoroethylene (ePTFE) and/or other flexible polymeric materials.

In general, embodiments of the self-expanding body frame 30 can provide a substantial radial force, while exhibiting a minimal lateral resistance to being collapsed to a low profile for placement in a delivery catheter. The radial force can be used to open or maintain a blood-flow path through or around a thrombus. The minimal lateral resistance to being collapsed is useful for positioning and repositioning the body frame 30 within the small diameter of a delivery catheter. Interstices in the body frame 30 provide open spaces between the strut elements 32 that can allow for portions of a thrombus to protrude within the interior of the body frame 30. Portions of thrombus in the interior of the body frame 30 can be removed by, for example, aspiration or maceration (as described below).

In some implementations, the body frame 30 may remain in a patient's vasculature only while the patient is undergoing a thrombectomy, and may generally remain coupled to support wire 15 throughout the treatment. The thrombectomy device 10 may be used to collect thrombotic material from the vasculature, so that the material may be safely removed from the vasculature, and may minimize a risk that the material may travel downstream of the device through the vasculature.

The filter bag 40 of the example thrombectomy device 10 can be attached to and extend from an end of the body frame 30. In some embodiments the filter bag 40 is attached to a distal end of the body frame 30. In some embodiments, the filter bag 40 can overlap a portion of the body frame 30, such as up to about one, or more than one, distal rows of strut elements 32 (see, e.g., FIG. 3), such that the body frame 30 provides a support structure underlying at least a portion of the filter bag 40. In some embodiments, the filter bag 40 does not overlap the body frame 30 and the filter bag 40 is unsupported other than by its attachment to the distal end of the body frame 30. U.S. Publication 2005/0177186 to Cully et al., which is hereby incorporated by reference in its entirety for all purposes, describes various filter bag embodiments and methods of making and using filter bags that can be applicable to the embodiments provided herein.

In some embodiments, the longitudinal length of the filter bag 40 is approximately proportionate to the length of the body frame 30. For example, in some embodiments the length of the filter bag 40 is less than or equal to about one-half of the length of the body frame 30. In some embodiments, the length of the filter bag 40 is about one-half of the length of the body frame 30 to about equal to the length of the body frame 30. In some embodiments, the length of the filter bag 40 is greater than the length of the body frame 30.

In general, filter bag 40 can capture and contain thromboemboli, plaque, and other particulate, while enabling pass-through flow of blood. The filter bag 40 can be made from a variety of filter media materials. For example, the filter media can be a laser perforated layer of thin polytetrafluoroethylene (PTFE). In some embodiments, the range of pore sizes of the filter media can be from 20-30 μm, 30-50 μm, 50-70 μm, 70-80 μm, or 80-100 μm. In some embodiments, the pore sizes of the filter media can differ depending on the region of the filter bag. In some embodiments, the filter media can be treated to become hydrophilic, such as by dipping the media in a heparin solution or polyvinyl alcohol solution. Treating the filter media with heparin solution can provide an additional benefit, in certain implementations, of inhibiting thrombus formation at holes in the media, which may enhance blood flow through the holes in the media.

FIGS. 2A-2I illustrate example devices, systems, and processes for treatment of thrombi. In general, the embodiments and concepts described can be applied in virtually any vascular region containing thrombi, for example, neurovascular, cardiovascular, and peripheral vessels, and in both arterial and venous vasculature systems. The embodiments and concepts described generally pertain to: (1) opening a blood-flow path through a vessel obstructed by a thrombus and (2) capturing and removing an amount of thrombotic material.

FIG. 2A illustrates an example vasculature portion 210 including a thrombus 230 at a thrombus site 235. The thrombus 230 can be, for example, attached to or lodged against a vessel wall 225, or lodged within a vessel 220. The thrombus 230 can partially or completely block the blood flow 226 through vessel 220. While the example of FIG. 2A depicts a thrombus 230 that partially blocks blood flow 226 through vessel 220, the devices and techniques described herein may also be used for clots or thrombi that completely block blood flow through a vessel.

Typically, access to the thrombus 230 can be initially achieved by a flexible guidewire 250. In some cases, other devices such as one or more guide catheters (not shown) may also be used to navigate through the patient's vasculature to a location near a target thrombus. In some cases, access to the thrombus can be achieved by the combination of one or more guide catheters and guidewires. For example, a combination of successively smaller guide catheters can be arranged in a telescope-like fashion. In some implementations, guidewire 250 can be inserted in vessel 220 so that the distal tip of guidewire 250 extends past the thrombus site 235.

FIG. 2B illustrates an example catheter 240 installed over the guidewire 250. The previously inserted flexible guidewire 250 can be used to pilot the insertion of the catheter 240 in an over-the-wire manner. In some applications, the catheter 240 can be a micro-catheter having an inner diameter of, for example, 0.021 inches or 0.027 inches. Proportionately larger catheters can be used in larger vessels as determined by a clinician operator. In some implementations, the catheter 240 can be advanced to a position so that its distal tip extends past the thrombus site 235.

FIG. 2C illustrates the removal of the guidewire 250 from the catheter 240. In this embodiment, the guidewire 250 aided the navigation of the catheter 240 to a desired position. With the catheter 240 in the desired position, the guidewire 250 can be removed to make room within the lumen of catheter 240 for insertion of other devices to treat the thrombus 230, and other vessel obstructions or conditions, according to some implementations. In some embodiments, the guidewire 250 is left in place, whereby the guidewire 250 can be used to faciliate additional deployment operations.

FIG. 2D illustrates the insertion of an example thrombectomy device 10 through the lumen of catheter 240. In this delivery configuration, the thrombectomy device 10 is in a collapsed state to fit within the lumen of catheter 240. In some implementations, the thrombectomy device 10 can be advanced so that at least its distal tip extends past the thrombus site 235. In some implementations, it may be desirable to position the thrombectomy device 10 such that a majority or substantially the entire filter bag 40 is located beyond (e.g., distal of) the thrombus 230.

While FIGS. 2A-2I depict an implementation in which the target thrombus 230 is generally concentric with the vessel 225, in some implementations a thrombus is eccentrically positioned within a vessel. That is, the location of the thrombus may be biased to a particular side of the vessel. In such implementations, the catheter 240 can be inserted around (rather than through) the thrombus. However, the principles of operation of the thrombectomy device 10 in the context of an eccentrically positioned thrombus are generally the same as described herein in relation to the concentric thrombus of FIGS. 2A-2I.

FIG. 2E illustrates an example thrombectomy device 10 in an expanded (e.g., deployed) configuration within a thrombus 230. In some implementations, this arrangement can be achieved by retracting the catheter 240 from the position shown in FIG. 2D, while maintaining or restraining the thrombectomy device 10 in its prior (e.g., as shown in FIG. 2D) axial position with respect to the thrombus 230. That is, the catheter 240 can be drawn backward (proximally) while holding the thrombectomy device 10 in place to cause the emergence of the thrombectomy device 10 from the lumen of the catheter 240.

As described previously, the body frame 30 of the thrombectomy device 10 can, in some embodiments, be self-expanding. That is, the body frame 30 can have a shape-memory characteristic that urges the frame to assume an expanded configuration (refer to FIG. 1) when it is unconstrained (e.g., unconstrained after emerging from a delivery catheter). In some embodiments, the body frame 30 may assume a partially expanded configuration when it is partially constrained (as by thrombus 230), as shown in FIG. 2E. In some embodiments, such as those with an open lattice construction, the body frame 30 can penetrate completely, or macerate, through at least a portion of thrombus 230 to come into contact with the inner vessel wall 225. In any case, the thrombectomy device 10 will expand such that the filter bag 40 will substantially make contact with the inner vessel wall 225 before the entirety of the body frame 30 is deployed. In that manner, one or more dislodged thrombotic fragments separated from the thrombus 230 by deployment of the body frame 30 can be captured by the filter bag 40.

The expansion of the thrombectomy device 10 as it exits the catheter 240 may open or enlarge a blood-flow 226 path through or around the thrombus 230, according to some implementations. In some embodiments, such as those with a relatively higher density of frame material, the body frame 30 can extert substantial radial force against the thrombus 230 to compact the thrombus 230 against inner vessel wall 225. That is, the radial force associated with the expansion of the body frame 30 can be exerted on the surrounding or adjacent thrombus 230 so as to displace or compact at least a portion of the thrombotic material, thereby opening or enlarging a blood-flow 226 path (also known as recanalization). In that case, the blood-flow 226 path can include a path through the inner region of the body frame 30. Hence, a blood-flow 226 path can be created or enlarged as a result of the displacement of the thrombotic material by the action of the expanding body frame 30. Because blood includes natural lytic agents, the creation or expansion of the blood-flow 226 path through the thrombus 230 may, in some embodiments, encourage additional reduction of the thrombus 230 as the blood's natural lytic agents work to attack the thrombus 230.

The proximal portion of the filter bag 40 can be in contact with the inner vessel wall 225. Thus, if thrombotic fragments are dislodged from the thrombus 230 as a result of the displacement or maceration of the thrombotic material by the body frame 30, the thromboemboli can be captured by the filter bag 40. For example, liberated thromboemboli may be carried by blood via the blood-flow path distally through the body frame 30 and into a space defined by the filter bag 40. The blood may then pass through the filter bag, for example through small pores in the filter bag, while the thromboemboli may be captured or trapped within the filter bag 40 because the thromboemboli may be too large to pass through the pores in the filter bag. In this manner, dislodged thrombotic fragments can be prevented from becoming fugitive thromboemboli within the bloodstream.

In the case of a neurological vascular thrombus occlusion, restoring perfusion as described above is an initial treatment pursuant to saving a patient's life. Restoring downstream perfusion, even if only partial perfusion, restores blood flow to downstream neurological tissues. Restoring blood flow may also minimize and/or eliminate the pressure of blood pushing on the thrombus 230 and the vacuum or negative pressure located just distally of the thrombus 230. The reduction or elimination of that pressure differential on the sides of the thrombus 230 can enhance the effectiveness of the thrombectomy device 10.

In some embodiments, the construction of the body frame 30 can permit some portions of the thrombus 230 to penetrate between the strut elements 32 to within the inner region of the body frame 30, as can been seen in FIG. 2E. The same can occur between the tethers 22, in some implementations. As described further below, the penetration of thrombotic material to within the body frame 30 and tethers 22 can allow for additional treatment procedures to reduce the size of the thrombus 230.

FIG. 2F illustrates some examples of the thrombectomy techniques that can be performed using the thrombectomy device 10. In particular, as a result of opening or enlarging a blood-flow path as described above, an increased amount of blood can then flow over the surface of the thrombus 230, thereby encouraging thrombolysis of thrombus 230. That is, causing additional blood to flow over the surface of the thrombus 230 can enhance the effects from blood's natural tendency to dissolve the thrombus. The blood's lytic action may partially erode surface 232 of thrombus 230 by dissolving some of the thrombus 230, or by dislodging some thrombotic particles. Dislodged thrombotic particles can be captured in filter bag 40 to prevent them from becoming thromboemboli in the bloodstream. One or more portions of thrombus 230 protruding through the tethers 22 and/or body frame 30 can be exposed to the increased blood-flow and potentially dissolved by the blood's lytic tendencies. In some examples, even portions of the thrombus 230 that do not protrude through a portion of the body frame 30 or the tethers 22 may be reduced in size or eliminated because of increased exposure to blood flow and the associated increased lytic action such increased exposure may provide to break down or dissolve the thrombus 230.

As can be seen with reference to FIG. 2F, device 10 is a single device delivered over a single catheter. Filter bag 40 is integral with body frame 30, being attached to a distal end of body frame 30 or overlapped with a portion of body frame 30 in some implementations. In some embodiments, no portion of filter bag 40 is directly attached to support wire 15. Moreover, device 10 includes only one attachment point to support wire 15 in some implementations, namely, via collar 18, which fixedly couples tethers 22 to the support wire 15.

FIG. 2G illustrates additional examples of thrombectomy techniques that can be performed by some embodiments of the thrombectomy device 10. Some techniques involve articulation and/or manipulation of the support wire 15 in various manners. Some techniques involve pushing the support wire 15 forward to advance the support wire 15 in the direction of arrow 17, which may advance collar 18 to a location interior of the body frame 30 (e.g., to a location within an interior region defined by body frame 30), or to a location within the filter bag 40 (e.g., to a location within an interior region defined by filter bag 40). In some embodiments, the advancing of the support wire 15 can be accomplished using, for example, a lead screw or lever device at an actuator coupled to the proximal end of the support wire 15. In other cases, the support wire 15 can be manually advanced by a clinician operator. In general, the body frame 30 and filter bag 40 may not substantially move longitudinally in relation to the vessel wall 225 in response to the support wire 15 and collar 18 being advanced. The body frame 30 and filter bag 40 remain substantially stationary longitudinally because of the interference fit of the body frame 30 with the thrombus, and because the tethers 22 can become everted as the support wire 15 is advanced.

In some embodiments, the one or more tethers 22 (some embodiments include a single tether, and some embodiments include more than one tether) can have shape-memory characteristics so that the one or more tethers 22 will automatically position themselves during deployment to the configuration approximately as shown. That is, in some embodiments the device will deploy, based on a shape memory property of the one or more tethers 22, so that the one or more tethers 22 are everted and substantially reside within a space defined by the body frame 30.

Because of the lengths of the individual tethers 22, which may in some embodiments have lengths at least about two times a diameter of an opening defined by the body frame 30 in an unconstrained state, advancing the collar 18 to a location interior of the body frame 30 may impart only a minimal force or substantially no force to the body frame 30 of the device, and thus the body frame 30 may generally maintain its position with respect to the thrombus 230 as the collar 18 is advanced. While the body frame 30 can, in some embodiments, remain stationary with respect to the thrombus 230, the central collar 18 and tethers 22 are advanced forward to positions within the interior of the body frame 30, and in some embodiments within the filter bag 40. In particular, the tethers 22 in this manner have been everted, for example, as disclosed in U.S. Publication 2005/0101989 describing looped support strut elements, the contents of which are incorporated herein in its entirety for all purposes, including for its discussion of making frame and strut structures.

Portions of the everted tethers 22 may be in close proximity to the body frame 30 of the thrombus treatment device. That is, as the everted tethers loop from a proximal end of the body frame 30 to the collar 18, a substantial portion of the tether may be adapted to reside adjacent or substantially adjacent an inward-facing portion of the body frame 30. In this configuration, the everted tethers 22 may make contact with portions of the thrombus 230 that have penetrated through the interstices of the body frame 30 to within the inner region of the body frame 30. In some embodiments, the effectiveness of this thrombectomy treatment can be enhanced by having long and flexible tethers 22 that are configured to make contact with all or a portion of the thrombus 230 in the inner region of the body frame 30. In some embodiments, the effectiveness of thrombectomy treatment can be enhanced by introducing an inflatable balloon device within the inner region of the body frame 30 that can be inflated to urge the tethers 22 into contact with all or a major portion of the thrombus 230 in the inner region of the body frame 30. In some embodiments, such a balloon device can be located on support wire 15, or in some embodiments it can be a separate complimentary device located on another support wire/tube.

In some embodiments, the balloon device is as described in the provisional Patent Application No. 61/678,898 titled "Space-Filling Device," having inventors Edward H. Cully and Michael J. Vonesh, filed on Aug. 2, 2012, and which is herein incorporated by reference in its entirety for all purposes.

With the everted tethers 22 in contact with portions of thrombus 230 in the interior of the body frame 30, the removal of some additional thrombotic material may be accomplished in the following manner. For example, the support wire 15 may be articulated and/or manipulated. In some cases, the support wire 15 can be rotated or twisted as indicated by arrows 16, alternatively clockwise and then counterclockwise (or vice versa), and, in some embodiments, repeated one or more times such that a rotational force is imparted from the support wire 15, through the collar 18, to the tethers 22. The tethers 22 or portions of the tethers 22 may thus rotate and act as cutting blades to sever, shave, or break apart portions of thrombus 230 that protrude through openings of the body frame 30. That is, the clinician operator can, manually or with the assistance of a mechanism, actuate a twisting motion at the proximal end of support wire 15 which translates to a twisting of the distal end of the support wire 15 and causes a swiveling or pivoting motion of a portion of the tethers 22, the force being applied to the tethers 22 only at one end of the tethers (the end coupled to the collar 18). In response, the tethers 22 will be swiveled to cut through some portions of thrombus 230 that are protruding through body frame 30.

For example, in some implementations the support wire 15 can be twisted approximately 180° or 270° clockwise from the neutral starting position, returned to the neutral starting position, and then 180° or 270° counter-clockwise from the neutral starting position. In some implementations, the rotation of the support wire 15 can be limited by having, for example, hard-stops to prevent rotation beyond that which the tethers 22 are capable of handling without imparting forces on the body frame 30 which could otherwise cause movement of the body frame 30. The hard stops may be incorporated, for example, by a hub device at a proximal end that includes a handle or knob that an operator or motorized element may move to rotate the support wire 15. In other examples, any appropriate amount of rotation can be applied (e.g., about 30°, 45°, 60°, 90°, 120°, 135°, 150°, 180°, 210°, 225°, 240°, 270°, 300°, 315°, 330°, 360°, or rotations in excess of 360°).

This rotary motion can be repeated as needed in attempt to ensure that all the thrombotic material that can be severed has been severed. However, in some implementations, a single twisting motion (or no twisting motion) may be all that is required to adequately sever the thrombotic material as needed. In some embodiments, depending on the length and flexibility of the tethers 22, the twisting actuation of the support wire 15 can be 360° or more. Thrombotic material that is severed can be captured by the filter bag 40 to prevent the severed material from becoming thromboemboli in the bloodstream. Alternatively or additionally, the severed thrombotic material may be collected and removed from the bloodstream using aspiration. The aspiration may be performed using the guide catheter that was used to deploy the thrombectomy device, or an additional aspiration catheter may be used.

Because of the lengths of the individual tethers 22, which may in some embodiments have lengths at least about two times a diameter of an opening defined by the body frame 30 in an unconstrained state, the rotational force applied to the support wire 15, and through the collar 18 to the tethers 22, may substantially dissipate over the length of the tethers so that only a reduced force, in some cases a minimal or substantially zero force, is transmitted to the body frame 30 of the thrombectomy device 10. In this manner, damage to the vessel wall may be minimized because the body frame may not substantially rotate or substantially move longitudinally as the support wire is rotated.

By using longer tethers 22, the everted tethers 22 can be positioned closer to the interior wall of the body frame 30 in some implementations. In some examples, the position of the central collar 18 may be within the interior of the filter bag 40. In some embodiments, substantially the entire inner wall of the body frame 30 can be contacted or nearly contacted by the everted tethers 22. In some embodiments, the tethers 22 can be manufactured with sharpened edges or with specialized cutting designs to improve their cutting abilities. The vessel wall 225 can be protected from potential trauma related to the removal of thrombotic material by the cutting action of the everted tethers 22 because the body frame 30 can act as a barrier between the vessel wall 225 and the tethers 22 to protect the vessel wall 225. Using this thrombectomy technique, at least some of the portions of thrombus 230 that are protruding within body frame 230 may be severed from the thrombus 230 and collected in the filter bag 40.

In some embodiments, rather than twisting the support wire 15 to cause the tethers 22 to sever portions of thrombus 230, the support wire 15 can be articulated and/or manipulated by advancing the support wire 15 proximally (in the direction of arrow 17) and withdrawing the support wire 15 distally to cause the tethers 22 to move and potentially sever portions of thrombus 230. The advancing and withdrawing movements (without substantially rotational movement) can be repeated as desired to cause the severance of some portions of thrombus 230.

FIG. 2H illustrates additional examples of thrombectomy techniques that may be performed by embodiments of the thrombectomy device 10. With the tethers 22 in the everted configuration, the catheter 240 (or another catheter) can be moved forward such that the distal tip of the catheter 240 is near to the tethers 22 or to the collar 18. Radiopaque markers that can be used, for example at or near the distal tip of the catheter 240, can enhance visualization of the position of the catheter 240. With the distal tip of catheter 240 near or inside of the interior of the body frame 30, additional treatment techniques can be possible. For example, the catheter 240 can be used for aspiration of the thrombus 230 or fragments of the thrombus 230. In general, aspiration can include applying a suction source to the lumen of catheter 240 so that portions of thrombus 230 can be removed from the thrombus site 235 by suctioning them into the lumen of catheter 240. In addition, a suction force applied via catheter 240 (or another catheter), may be used to aspirate thrombotic material that has collected within the filter bag 40 prior to removal of the thrombectomy device 10. Removal of the embolic load prior to removal of the thrombectomy device 10 can minimize the risk of releasing those emboli during the thrombectomy device 10 retrieval procedure.

The position of the tip of catheter 240 also lends itself to being used as a conduit to deliver one or more thrombolytic pharmacological agents directly to or near to the thrombus 230.

Thrombotic material that is dislodged by these techniques can be captured by the filter bag 40 to prevent the dislodged material from becoming thromboemboli in the bloodstream.

FIG. 2I illustrates an example of the removing the thrombectomy device 10 from the thrombus site 235. As the thrombectomy device 10 is removed from the vessel 220, some remaining thrombotic material from thrombus 230 may be pulled along with the body frame 30 or tethers 22. As a result of the thrombectomy techniques performed by the thrombectomy device 10, in some cases, only the eroded surface 232 of the previous thrombus 230 may remain at the thrombus site 235, or, in some cases, substantially no thrombotic material may remain. The removed thrombotic material can have been captured by the filter bag 40 and removed from the patient's vasculature by suction as described above or by being retained in the filter bag 40, in some implementations.

Figure 3:
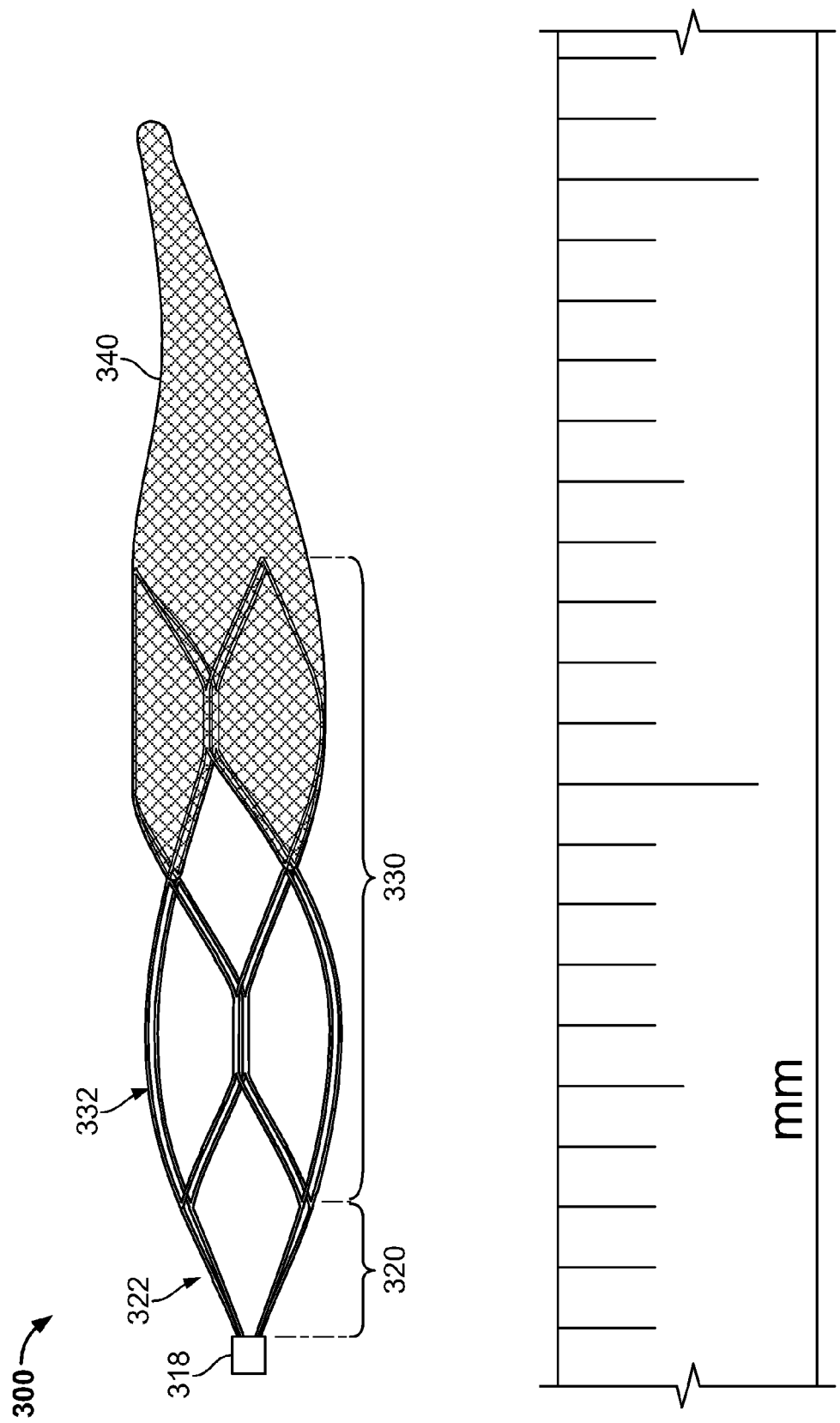
FIG. 3 is a photograph of an embodiment of an example thrombectomy device.

FIG. 3 depicts an example thrombectomy device 300. This particular example thrombectomy device is sized approximately for a small vessel, such as a vessel to be treated as part of a neurovascular thrombectomy procedure. As can be seen, the length of the body frame 330 is about 15 mm and the outer diameter of the body frame 330 is about 5 mm. Thus, the ratio of the length of the body frame 330 to the diameter of the body frame 330 is about 3:1, with the thrombectomy device 300 in an expanded and unconstrained state. In some embodiments, the ratio of the outer diameter to the length of an expanded and unconstrained body frame is about 4:1, about 5:1, about 6:1, about 7:1, or about 8:1, or more.

The thrombectomy device 300 exhibits many of the components described above. For example, the tether assembly 320 includes tethers 322 that are coupled on one end with a central collar 318 and with a body frame 330 on the opposite end. The body frame 330 includes rows of strut elements 332. In this embodiment, there are three (3) rows of strut elements 332. The open-faced cells of the strut elements 332 are configured generally in diamond shapes. A filter bag 340 extends from the body frame 330. In this example, the filter bag 340 overlaps one (generally diamond-shaped) circumferential ring of strut elements 332 of the body frame 330. In other examples, the filter bag 340 may extend from a distal end of the body frame 330 without overlapping the body frame 330. In some embodiments, the length of the filter bag 340 is less than or equal to one-half of the length of the body frame 330. In some embodiments, the length of the filter bag 340 is greater than one-half of the length of the body frame 330.

Figure 4:
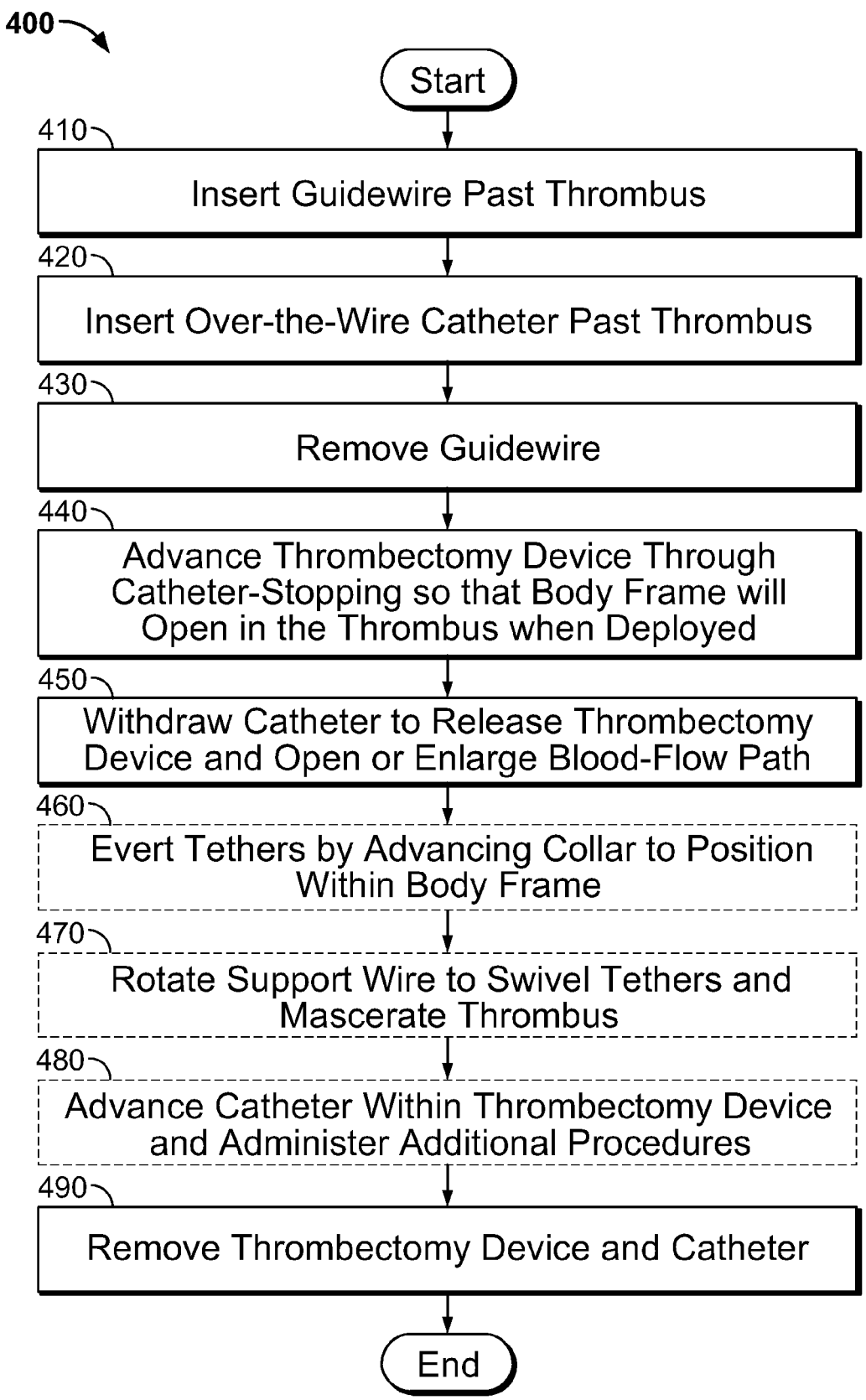
FIG. 4 illustrates an example embodiment of a method for performing a thrombectomy procedure.

FIG. 4 depicts an example embodiment of a method 400 for thrombectomy. At operation 410 a guidewire can be inserted through a patient's vasculature such that the distal end of the guidewire extends past the target thrombus to be treated. In some cases, one or more guide catheters can be used to assist with the placement of the guidewire. At operation 420 an over-the-wire catheter can be inserted over the guidewire. The catheter can be positioned so that its distal tip extends beyond the target thrombus to be treated. At operation 430 the guidewire can be removed through the lumen of the catheter. The catheter can remain in position with its distal tip extending beyond the target thrombus. At operation 440 a thrombectomy device, such as thrombectomy device 10 or 300 described above, can be advanced through a lumen of the catheter. The thrombectomy device, while still in the catheter, can be approximately positioned so that at least a portion or the entire filter bag is beyond the target thrombus.

In some implementations, the device can be positioned or aligned so that, on deployment, the body frame of the device will open within the thrombus. For example, a distal edge of the body frame may be aligned longitudinally with a distal end of the thrombus, so that the filter bag portion of the device may be located distal of the thrombus. In some examples, the distal end of the body frame may be positioned or aligned slightly distal of the distal end of the thrombus.

At operation 450, while maintaining the position of the thrombectomy device, the catheter can be withdrawn, causing the thrombectomy device to exit the lumen of the catheter. The catheter may be withdrawn, for example, at least to a point where the proximal portion of the device body of the thrombectomy device is outside of the catheter lumen, or to a point where the body frame, tethers, and collar have exited the catheter lumen.

Since the thrombectomy device can, in some embodiments, be self-expanding, the withdrawal of the catheter can cause the thrombectomy device to expand as a result of being unconstrained from the catheter. When the thrombectomy device expands within or adjacent to the target thrombus, the device can open or expand a blood-flow path through or around the target thrombus, based on an outward radial pressure that the body frame of the device may apply against the thrombus when the device expands. If any thrombotic fragments are produced as a result of the force applied by the expanding of the device upon the target thrombus, the thrombotic fragments can be captured in the filter bag of the thrombus treatment device. The expansion of the thrombectomy device can cause some portions of the target thrombus to penetrate through the body frame of the thrombus treatment device. The increased blood flow resulting from operation 450 can enable the blood to perform natural thrombolysis to potentially reduce the size of the target thrombus. If thrombotic fragments are produced they can be collected in the filter bag of the thrombus treatment device.

Operation 460 is an optional act, wherein the collar can be advanced to a position within in internal region defined by the body frame of the thrombectomy device, which can evert the tethers of the device. This step can be taken, for example, for embodiments where the tethers 22 deploy in an uneverted configuration so that on deployment the collar 18 and the tethers 22 are located proximal of the body frame (see, e.g., FIGS. 1 and 3). The tethers of the thrombectomy device can thus be everted and thereby positioned generally within or substantially within the interior region of the body frame of the thrombectomy device. By bringing the collar and all or a portion of the tethers within a region defined by the body frame of the device, access possibilities for providing adjunct therapies or procedures may be enhanced. For example, one or more catheters may be advanced to a location within the body frame of the device, and hence to a position of close proximity to the thrombus, which may permit various adjunct therapies or actions that might not be possible for devices that cannot evert the tethers in this manner. In some examples the tethers can be everted so that a portion of the tethers extend within a region defined by the filter bag of the thrombus treatment device. As described above, in some implementations the tethers can be adapted to deploy in an everted configuration, for example based on a shape memory property of the tethers.

Whether the collar is positioned in a space interior of the body frame or interior of the filter bag, in some implementations the everted tethers can be used to sever, shave, or break apart portions of the target thrombus that may be protruding through and into the interior of the body frame, indicated at optional act 470. The thrombus portions can be severed, for example, as at least a portion of the tether is caused to move and contact the thrombus portion, whereby the tether may thereby cut through the thrombus portion and separate it from the thrombus. A rotational or twisting action may be applied to the support wire of the thrombectomy device, which may impart a twisting force through the collar to the tethers so that the tethers are twisted or caused to move in a swiveling or pivoting motion while the body frame and filter bag remain generally stationary. Any thrombotic fragments created from the maceration can be collected by the filter bag of the thrombus treatment device.

In some examples, everting the tethers 22, either on deployment or subsequently by advancing collar 18 to a position within the device, may cause portions of the thrombus to be severed without separately imparting a rotational force on the support wire 15. That is, the tethers may act to slice through the thrombus in some embodiments based on a longitudinal advancement of the support wire and collar, or even during deployment, whether they deploy as everted (e.g., being substantially within an area defined by the body frame) or otherwise. In some examples, the support wire can be repetitively advanced and withdrawn in a longitudinal direction, one or more times, to sever portions of the thrombus.

Operation 480 is an optional act, where the catheter can be moved distally so that its distal tip is approximately within the interior of the body frame. In this position, a lumen of the catheter can be used to aspirate the target thrombus, as by applying a suction force to the lumen from the proximal end of the catheter. The suction force may aspirate thrombotic material that dislodges from the thrombus as a result of the suction force, as a result of maceration of the thrombus by the tethers, or as a result of radial force imparted on the thrombus by the body frame of the thrombectomy device. The suction force may also aspirate thrombotic material that has collected in the filter bag of the thrombus treatment device. The same or another lumen of the catheter (or another catheter) can also be used, alternatively or additionally, to deliver one or more thrombolytic pharmacological agents proximately (e.g., from a location interior of a space defined by the thrombus) to the target thrombus. Again, any thrombotic fragments created from these actions can be collected by the filter bag of the thrombectomy device.

At operation 490 the thrombectomy device and the catheter can be removed from the patient's vasculature. The removal of the thrombectomy device may cause the removal of additional portions of the target thrombus, which may collect in the filter bag of the device, or remain attached to the tethers of body frame. The removal can be performed while applying a suction force to a lumen of the catheter so that any dislodged thrombotic material may be aspirated, and any remaining material that has collected in the filter bag can be aspirated. In some implementations, a proximally directed force may be applied to the support wire while holding the catheter in a constant position, and the thrombectomy device may be pulled into a lumen of the catheter. The thrombectomy device may collapse to the delivery configuration described previously within the lumen of the catheter, and the catheter and device may be withdrawn from the body or repositioned at the same or a different target thrombus.

FIG. 5A illustrates an example thrombectomy system 500. The thrombectomy system 500 is generally a system for performing maceration and aspiration of thrombi. This system can be delivered percutaneously and through a patient's vasculature to the site of a thrombus, such as a neurovascular, cardiovascular, or peripheral vein thrombus site. The thrombectomy system 500 may be used in both antegrade and retrograde applications.

The example thrombectomy system 500 can generally include a stabilization device such as a thrombus displacement device 550, a catheter 540, and a maceration device with two (2) primary components: (i) a tether assembly 520 comprising one or more tethers 522, and (ii) a body frame 530. In some embodiments, the tether assembly 520 and the body frame 530 can be constructed and configured as the tether assembly 20 and the body frame 30 described above in regard to example thrombectomy device 10. In some embodiments, the body frame 530 can include a membranous outer covering that comes into contact with the inner vessel wall. However, generally no filter bag is attached to the body frame 530.

The thrombus displacement device 550 may be any type of stabilization device that can be used to urge the thrombus 535 toward the maceration device, and generally minimize or prevent portions of the thrombus 535 from exiting distally of the thrombus displacement device 550. In some implementations, the thrombus displacement device 550 may be a balloon device. In other implementations, the thrombus displace device 550 may be an actuatable braid structure, a filter-like device, a corkscrew-like coil structure, a basket structure, an occluder disc, a malecot device (e.g., a longitudinally lanced tubular shape which, when axially compressed, takes on a fusiform shape as its arms deflect outwardly), or other types of suitable devices.

For simplicity, the discussion that follows will assume a balloon device is the thrombus displacement device 550. Thrombus displacement device 550 can include a tube 555 and a balloon 560. The tube 555 can convey a suitable inflation medium (e.g., a fluid, gel, gas, solid, foam, etc.) to the balloon 560 to inflate the balloon 560 and can control the axial position of the balloon 560 within the vessel 510. In some embodiments, the inflation medium includes a contrast media to facilitate radiographical visualization of the balloon 560. The thrombus displacement device 550 can be collapsible for delivery via a tube, such as support tube 515. Alternatively, the thrombus displacement device 550 can be delivered by another catheter that may or may not be inserted through catheter 540. Although a balloon configuration is described herein, any suitable stabilization device that can cross at least a portion of the thrombus may be used.

The maceration device, including the tether assembly 520 and the body frame 530, is collapsible for delivery via a catheter, such as catheter 540. The body frame 530 can be self-expanding as described above regarding the body frame 30. The maceration device can further include a support tube 515 that may be generally analogous to the support wire 15 described above. The support tube 515 can be used to push and thereby deploy the collapsed maceration device through its delivery catheter, generally analogous to the manner described above regarding FIGS. 2D-2E. However, in this embodiment the location of the expanded body frame 530 can be adjacent to (e.g., located proximally of) the target thrombus, rather than within the thrombus.

The support tube 515 can also be used to evert the tether assembly 520 as by advancing a central collar 518 (generally analogous to collar 18 described above) to a position within the body frame 530, and can be rotated to cause a swiveling or pivoting motion at the tethers 522. The central collar 518 can be used to couple the tether assembly 520 to the support tube 515. The maceration device is collapsible so it can be contained within the lumen of catheter 540 for delivery through the patient's vasculature to the location adjacent to a target thrombus 535. At or near, or, in some embodiments just proximal to the thrombus site, the maceration device can be deployed outwardly from the distal tip of the delivery catheter 540, at which time the maceration device can expand to the unconstrained configuration shown in FIG. 5A. The radial force of the self-expanding body frame 530 can effectively anchor (temporarily) the body frame 530 to the interior wall of vessel 510 via an interference fit.

While FIG. 5A depicts a particular maceration device embodiment having the distal ends of the tethers 522 coupled to the proximal end of the body frame 530 and the proximal ends of the tethers 522 coupled to a collar 518 that is coupled to a support tube 515, in another embodiment the distal ends of the tethers 522 can be coupled with the distal end of the body frame 530.

Some embodiments can include two sets of tethers, one set extending from the proximal end of the body frame 530 (as shown in FIG. 5A) and the second set extending from the distal end of the body frame 530 (not shown). Some embodiments including two sets of tethers can include a single support tube 515 which can include two collars for coupling the two sets of tethers to the support tube 515, in some examples. In this example, rotation of the support wire may cause both sets of tethers to be moved (e.g., in a swiveling or pivoting motion), for example, and each set of tethers may assist in severing, shaving, or breaking up the thrombus.

Some embodiments that include two sets of tethers can include two support tubes located coaxial to each other, where one set of tethers may be coupled with a first support tube (e.g., by a first collar), and the second set of tethers may be coupled with a second support tube (e.g., by a second collar). In this example, one or both of the support tubes may be rotated, or counter-rotated with respect to each other to cause movement (e.g., in a swiveling or pivoting motion) of the associated sets of tethers for severing, shaving, or breaking up the thrombus, for example. For example, if a single support tube is rotated and the other support tube is not rotated, the set of tethers corresponding to the rotated support tube may be caused to move (e.g., in a swiveling or pivoting motion), while the set of tethers corresponding to the non-rotated support tube may remain stationary. In this example, the interaction of the tethers may cause severing, shaving, or breaking up the thrombus.

In some examples, each of the first set and the second set of tethers is everted. In some examples, the proximal set of tethers is caused to swivel or pivot while the distal set of tethers remains stationary. In some examples, the distal set of tethers is caused to swivel or pivot while the proximal set of tethers remains stationary. In some examples, both the distal set of tethers and the proximal set of tethers are caused to rotate or pivot, and in these examples the tether sets may be caused to swivel or pivot in the same direction, or in opposite directions, for example. In general, rotation of the support tube or tubes may be done similarly to the rotation of support wire 15, as described above. Since the support tubes provide a through-lumen, guidewires and/or thrombus stabilization devices can be inserted and removed as necessary prior to and during the procedure.

FIG. 5B illustrates the example thrombectomy system 500 wherein the tether assembly 520 has been everted, either by advancing the collar 518 to a position interior of the frame 530 or on deployment based on a shape memory property of the tethers 522, to a maceration configuration. In the maceration configuration, the tether assembly 520 can be substantially located within the interior of the body frame 530. This configuration is the result of pushing the support tube 515 forward (distally) within the catheter 540 or in conjunction with the catheter 540, which causes advancement of the collar 518 and the distal ends of the tethers. The flexibility of the tethers 522 can allow the tether assembly 520 to become everted. The body frame may 530 remain stationary with respect to the vessel 510 during the movement of the support tube 515 and tether assembly 520 to the maceration configuration. That is, the body frame 530 may not experience substantial movement in a rotational, linear translational, or any other types of movements. In the alternative embodiments having the tethers attached to both ends, the tethers at the distal end of the body frame 530 could be everted by applying tension to their corresponding support tube. Moreover, in some embodiments, tension can be applied to the distal most support tube while simultaneously moving the proximal-most support tube forward, thereby everting both sets of tethers.

FIGS. 5C-5E illustrate end views (as depicted by view "A-A" in FIG. 5B) of the tethers 522 within the body frame 530. In general, these three (3) views depict the articulation and/or manipulation of support tube 515 by inducing a swiveling or pivoting action of the tethers 522 during the maceration process. As described below, in some embodiments the swiveling movements of the tethers 522 can sever, shave, or break apart portions of the thrombus 535 for removal by aspiration by catheter 540. In some implementations, FIGS. 5C-5E depict views of the tethers 22 of the thrombectomy device 10 described at FIG. 1 and at FIG. 2G.

FIG. 5C depicts an example configuration of the tethers 522 in their neutral position or generally relaxed condition. As can be seen in FIG. 5C, in some embodiments the tethers 522 can have a generally looped shape in the neutral position. In some examples, the tethers 522 may have a generally "S" shape in the neutral position.

FIG. 5D depicts an example configuration, which may represent a first torqued position, of the one or more tethers 522 after the support tube 515 has been rotated in the clockwise direction as indicated by arrow 570. As can be seen in FIG. 5E, the tethers 522 generally have a first linear shape in the first torqued position. FIG. 5E depicts an example configuration, which may represent a second torqued position, of the tethers 522 after the support tube 515 has been rotated in the counterclockwise direction as indicated by arrow 575. As can be seen in FIG. 5E, the tethers 522 generally have a second linear shape in the second torqued position.

The maceration action of the one or more tethers 522 on the thrombus 535 can be created, in some implementations, by rotating support tube 515 clockwise and counterclockwise (back and forth, repeating as desired). In this manner, the tethers 522 may transition from their configuration in FIG. 5D to FIG. 5E, and back again to FIG. 5D, and then again to FIG. 5E, and so on. In other cases, a single rotation (or no rotation, i.e., solely a longitudinal motion to thereby articulate and/or manipulate the support tube 515) may be enough for the tethers 522 to adequately macerate the thrombus to the extent determined necessary by the clinician operator. In some implementations, the rotation of the support tube 515 can be limited by having, for example, hard-stops to prevent rotation beyond that which the tethers 522 are capable of handling without imparting forces on the body frame 530 which could otherwise cause movement of the body frame 530 in relation to vessel 510, in manners similar to those discussed above with reference to device 10. In some embodiments, the tethers 522 can sweep through a range of motion of up to 180 degrees without causing a substantial rotational or longitudinally translational motion of the body frame 530 in relation to vessel 510. In some embodiments, the tethers 522 can sweep through a range of motion of up to 270 degrees without causing a substantial rotational or longitudinally translational substantial motion to the body frame 530 in relation to vessel 510. In some embodiments, the tethers 522 can sweep through a range of motion of up to 360 degrees without causing a substantial rotational or longitudinally translational motion of the body frame 530 in relation to vessel 510. In some embodiments, the tethers 522 can sweep through a range of motion of up to 540 degrees without causing a substantial rotational or longitudinally translational motion of the body frame 530 in relation to vessel 510. In some embodiments, the tethers 522 can sweep through a range of motion of equal to or greater than 540 degrees without causing a substantial rotational or longitudinally translational motion of the body frame 530 in relation to vessel 510.

FIG. 5F illustrates the maceration process of example thrombectomy system 500. The maceration process is generally performed by the swiveling of the one or more tethers 522 that may contact portions of the thrombus 535 to cut portions of the thrombus 535 into thrombus fragments 535' which can be aspirated by catheter 540. The swiveling motion of the tethers 522 that may cause the tethers 522 to act as cutting blades has been described above in regard to FIGS. 5B-5E. In some embodiments, the swiveling tethers 522 can come into contact with thrombus 535 by the urging of the balloon 560 on the thrombus 535. That is, the thrombus displacement device 550, which may be attached to a support wire, can be pulled by a clinician operator to force the thrombus 535 into the interior of the body frame 530 and into contact with the tethers 522 as they are being swiveled. In this manner, portions of the thrombus 535 can be severed into thrombus fragments 535'. In other embodiments, the stabilization device can remain stationary and the masceration device can be advanced towards the thrombus 535 to perform masceration of the thrombus 535.

The one or more thrombus fragments 535' can be removed from the vessel 510 by an aspiration device, such as catheter 540 or another aspiration device. Catheter 540 may also be the delivery catheter for thrombectomy system 500. The maceration process can continue by gradually pulling the thrombus displacement device 550 while motioning tethers 522 (e.g., by rotating tube 515). These operations can be performed manually or with the assistance of mechanical or electromechanical devices. Depending upon the consistency of the thrombus, the act of pulling and forcing the thrombus through the tethers may be enough to sever the thrombus into aspiratable-sized portions without causing motion of the tethers. That is, in some cases when the thrombus is soft enough, the tethers may not need actuation to sever and aspirate the thrombus.

While the maceration is taking place, the wall of vessel 510 may be protected from potential trauma from the tethers 522 because of the presence of the body frame 530. The body frame 530 acts as a protective barrier between the tethers 522 and the inner wall of vessel 510. The body frame 530 of some embodiments may also include a covering (not shown) such as an ePTFE tubular covering which could also assist in protecting the host vessel from undue trauma during the maceration process. Also, because of the lengths of the individual tethers 522, which, in some embodiments, may have lengths at least about two times a diameter of an opening defined by the body frame 530 in an unconstrained state, the rotational force applied to the support tube 515, and through the collar 518 to the tethers 522, may substantially dissipate over the length of the tethers so that only a minimal force or substantially zero force is transmitted to the body frame 530 of the device. In this manner, damage to the vessel wall may be minimized because the body frame may not rotate or move as the support tube 515 is rotated, for example.

At the completion of the maceration process, the rotation of the support tube 515 and the linear motion of the thrombus displacement device 550 can be ceased. Prior to removal of the thrombectomy system 500 from vessel 510, the maceration device can be retracted within the catheter 540. Also, the balloon 560 can be deflated and retracted back through the lumen provided by the support tube 515. The thrombectomy system 500 can then be removed from the patient's vasculature.

FIG. 6A illustrates an example thrombectomy device 600. This device can be delivered percutaneously and through a patient's vasculature to the site of a thrombus, such as a neurovascular, cardiovascular, or peripheral vein thrombus site. The thrombectomy device 600 may be used in both antegrade and retrograde applications.

The example thrombectomy device 600 is generally a device for treating a target thrombus by opening or enlarging a blood-flow path through the thrombus, enabling natural thrombolysis via increased blood flow, and performing maceration of a thrombus while capturing thromboemboli in a filter bag. In general, the thrombectomy device 600 includes a body frame 630, a filter bag 640, and a tether assembly with two primary components: (i) tethers 625 and (ii) tether frame 620. The body frame 630, filter bag 640, delivery catheter 610, and support wire 655 are analogous to their corresponding components as described above. However, the tether assembly of thrombectomy device 600 can have a different arrangement as compared to previously described embodiments.

In some embodiments, the tether frame 620 can have multiple individual elongate arms that are each attached at one of their ends to a central hub 618. The central hub 618 can serve to couple the tether frame 620 to the support wire 655. The individual arms of tether frame 620 can extend radially from the central hub 618 in a manner analogous to, for example, the spokes of a wheel. In some examples, the individual arms of the tether frame 620 may extend from the hub 618 without crossing or overlapping one another. In some examples, the individual arms may extend from the hub 618 and may cross or overlap one or more of the other arms, analogous to spokes of a bicycle wheel, for example.

The opposite ends of the individual arms can be attached to individual tethers 625. In some embodiments, the number of individual arms corresponds with the number of individual tethers as required for the particular configuration of the body frame 630 of the thrombectomy device 600. The tether frame 620 can be constructed from materials such as nitinol, titanium, stainless steel, various polymers, or a combination or sub-combination of materials.

The tethers 625 can be attached on their proximal ends (as shown in FIG. 6A) to the tether frame 620 and at their distal ends to the frame body 630. The tethers 625 can be, for example, thin flexible members with low column strengths. For example, the tethers 625 can be in the form of wires, fibers, filaments, membranes, strings, and/or threads. The tethers 625 can be constructed from various materials such as PTFE, other polymers, or from metals such as nitinol, titanium, and stainless steel, or a combination or sub-combination of materials.

The thrombectomy device 600 can be delivered to the site of a target thrombus 650 within the lumen of a catheter 610. The thrombectomy device 600 can be deployed from the catheter 610 such that the frame body 630 engages with the target thrombus 650. As described above with reference to frame body 30, the frame body 630 can act on the thrombus 650 to open or enlarge a blood-flow path. With increased blood flow, the natural lytic action of blood flow on the thrombus 650 can be enhanced to reduce the thrombus 650. Particles of dislodged thrombotic material can be captured in the filter bag 640 to prevent thromboemboli from being released into the vasculature.

FIG. 6B illustrates the example thrombectomy device 600 arranged in a maceration configuration. The thrombectomy device 600 can be arranged in the maceration configuration, for example, by advancing the support wire 655 distally, as represented by arrow 617. As the support wire 655 is pushed distally, the hub 618 and tether frame 620 are similarly advanced distally, while the body frame 630 remains in a substantially stationary position (e.g., no substantial rotational or translational movements) with respect to the vessel, allowing the tether frame 620 to be moved into the interior region of body frame 630.

In some embodiments, the diameter of the tether frame 620 can be smaller than the inner diameter of the body frame 630 so that the tether frame 620 can fit inside of the body frame 630. As the tether frame 620 moves into the interior of the body frame 630, the tethers 625, due to their flexibility, can be pulled along by the movement of the tether frame 620. In this manner, the tether frame 620 and the tethers 625 can be positioned within the interior of the body frame 630. Further, the tethers 625 can be positioned substantially parallel and adjacent to the inner wall of the body frame 630 in preparation for maceration of the thrombus 650.

The thrombus maceration process can be performed by rotating the support wire 655 as indicated by arrows 616. The motion imparted by the support wire 655 to the tethers 625 can cause the tethers 625 to act as thrombus shearing arms or blades. The clinician operation can actuate, manually or with device assistance, a rotary action of the support wire 655 in a manner similar to description above in regard to FIGS. 5B-5E. In some implementations, the rotation of the support wire 655 can be limited by having, for example, hard-stops to prevent rotation beyond that which the tethers 625 are capable of handling without imparting forces on the body frame 630 which could otherwise cause movement of the body frame 630. The body frame 630 can protect the vessel wall from potential trauma from the maceration process. Particles of dislodged thrombotic material can be captured in the filter bag 640 to prevent thromboemboli from being released into the vasculature.

Figure 7:
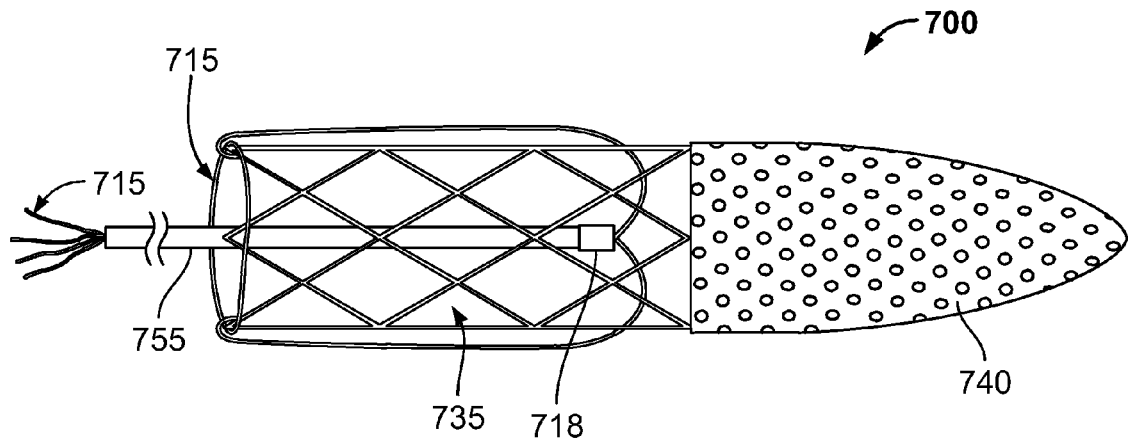
FIG. 7 illustrates an example thrombectomy device.

FIG. 7 illustrates an example thrombectomy device 700. This device can be delivered percutaneously and through a patient's vasculature to the site of a thrombus, such as a neurovascular, cardiovascular, or peripheral vein thrombus site. The thrombectomy device 700 may be used in both antegrade and retrograde applications. The thrombectomy device 700 is generally a device for treating a target thrombus by opening or enlarging a blood-flow path, enabling natural thrombolysis via increased blood flow, and performing maceration of a thrombus while capturing thromboemboli in a filter bag.

In general, the example thrombectomy device 700 includes a body frame 735, a filter bag 740, a support tube 755, and tethers 715. The body frame 735 and filter bag 740 are analogous to their corresponding components as described above. However, the tethers 715 and the support tube 755 of thrombectomy device 700 can have a different arrangement as compared to previously described embodiments.

The tethers 715 can be flexible strings, wires, threads, fibers, or the like, and made from a polymeric material such as PTFE, nylon, or polyester, or from a metallic material such as nitinol. The proximal ends of the tethers 715 can be arranged so that they are accessible to be controlled by a clinician operator, as shown at the left side of FIG. 7, where they may exit a lumen of the tube 755. The tethers 715 can be routed through the lumen of the support tube 755. The tethers 715 can exit the support tube 755 near the central collar 718 and be routed approximately radially outward and through the body frame 735 structure near the distal end of the body frame 735. From there (the distal end of the body frame 735), the tethers 715 can be routed proximally towards the proximal end of the body frame 735. For example, the tethers 715 can be woven among the structural members of the body frame 735 as the tethers 715 are routed towards the proximal end of the body frame 735. In some examples, the tethers 715 may be wound through cells of the body frame 735 as the tethers are routed from the distal end of the body frame to the proximal end of the body frame. In some examples, and as shown in FIG. 7, the tethers 715 can be routed from near the distal end of the body frame 735 to the proximal end of the body frame outside of the body frame (e.g., generally outside of a space defined by the body frame 735).

In some embodiments, when the routing of the tethers 715 reaches the proximal end of the body frame 735, the individual tethers 715 can be routed around the proximal circumference of the body frame 735—so that each individual tether 715 makes a loop or "lasso" around the proximal circumference of the body frame 735. The individual tethers 715 can then be attached to the body frame 735 (e.g., slip knots can be used). When the tethers 715 are pulled in a proximal direction at their proximal ends (e.g., by an operator), the distal and proximal ends of the body frame 735 can be deflected or collapsed inward towards the support tube 755. In this manner, a clinician operator can enable recapture of the thrombectomy device 700. That is, applying tension to the tethers 715, manually or with a device, can collapse the profile of the distal and proximal ends of the body frame 735 so that it can more easily enter within the lumen of a catheter (not shown in FIG. 7).

In some embodiments, when the routing of the tethers 715 reaches the proximal end of the body frame 735, the individual tethers 715 can make a partial loop around the proximal end of the body frame 735. For example, for a tether arriving at the proximal end of the body frame near a particular cell of the body frame, the tether may be routed circumferentially around the proximal end of the body frame and attached to a support member of an adjacent cell of the body frame. The individual tethers 715 can then be tied to the body frame 735 in locations on the body frame 735 so that the individual tethers 715 cooperatively form one single loop, or lasso, around the circumference of the proximal end of the body frame 735.

In some examples, collar 718 may be omitted. For example, the tethers 715 may exit a distal end of the tube 755. As another example, the tube 755 may include apertures (e.g., one aperture for each tether) in a side wall of the tube 755 near a distal end of the tube, and the tethers could exit the tube via the apertures.

As illustrated by example thrombectomy device 700, the tethers of the thrombectomy devices provided herein can extend from various locations on the body frames. In most of the example thrombectomy devices provided herein, the tethers are depicted as extending from the proximal end of the body frame. However, it should be understood that the tethers can extend from various other locations on the body frame. For example, in some embodiments, the tethers extend from the distal end of the body frame. In some embodiments, the tethers extend from a location between the proximal and distal ends of the body frame. In some embodiments, the individual tethers of a single thrombectomy device extend from different locations on the body frame, such as from the proximal end, distal end, or locations between the proximal and distal ends.

Figure 8:
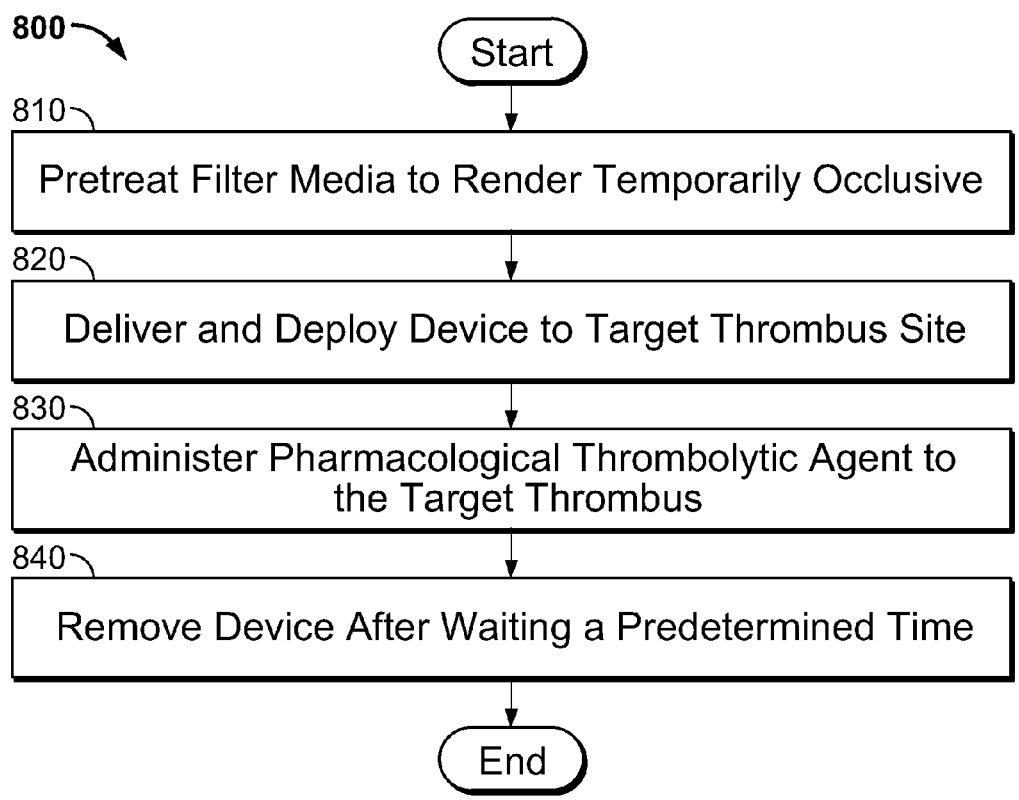
FIG. 8 illustrates an example embodiment of a method for performing a thrombolysis procedure.

FIG. 8 depicts an example embodiment of a method 800 for thrombolysis. In general, this method can be used to enhance the effectiveness of a pharmacological thrombolytic agent that can be delivered to a target thrombus. At operation 810 the filter bag of a thrombectomy device (e.g., device 10, 300, 600, or 700) can be treated with autologous blood or a thrombogenic material to "pre-clot" the filter media, i.e., to make the filter bag temporarily occlusive to blood flow. For example, in some implementations the filter bag can be soaked in autologous blood, or a stagnant thrombogenic solution or gelatin, prior to deployment so that the blood or other material clots within the small holes of the filter bag. In some implementations, autologous blood or thrombogenic material can be aspirated into the delivery catheter to make it come in contact with a filter bag that is within the delivery catheter. In some implementations, autologous blood or thrombogenic material can be injected through a catheter to make it come in contact with an in situ filter bag that has been deployed in a vessel. The device receiving the pre-clotting treatment can be any thrombectomy device that uses a filter bag, including but not limited to the thrombectomy devices described above.

At operation 820 the device can be delivered to and deployed at the target thrombus site. As described above, the device may be deployed so that the (pretreated) filter bag is positioned distally of the target thrombus (e.g., distally of and adjacent to the thrombus). At operation 830 a pharmacological thrombolytic agent can be delivered to the target thrombus. For example, the thrombolytic agent (e.g., tPA) can be injected to the bloodstream area of the target thrombus via a catheter or hypotube. In some embodiments, the catheter used to deliver the thrombectomy device can also be used to deliver the thrombolytic agent. Or, the lumen of the delivery catheter can be used to route an additional drug delivery tube to the site of the target thrombus. In some implementations, the thrombolytic agent can be delivered via a catheter that is advanced so that the distal end of the catheter is interior of the body frame of the device, thereby releasing the thrombolytic agent within a space defined by the clot itself when the body frame is positioned within the clot.

Because the pretreated filter bag may act as a temporary occluder, restricting blood flow through the device, the administered thrombolytic agent may remain concentrated at or near the thrombus site, which may enhance the action of the thrombolytic agent in dissolving the thrombus, and may prevent the thrombolytic agent from dispersing systemically into the vasculature of the patient for a period of time.

At operation 840, the thrombectomy device can be removed, for example after waiting a predetermined time. The filter bag, having been pretreated to make it more occlusive to blood flow, can cause the thrombolytic agent delivered to the target thrombus to dwell in the area of the target thrombus—rather than being promptly flushed away by blood flow. That additional dwell time of the thrombolytic agent in the area of the target thrombus can enhance the effectiveness of the thrombolytic agent's thrombolytic action on the target thrombus. Hence, operation 840 prescribes waiting a predetermined time. Eventually the thrombolytic agent, which can also act to deplete the thrombogenic material on the pretreated filter bag, may substantially dissolve the thrombogenic material on the filter bag. That is, while the thrombolytic agent is dwelling in the target thrombus area, the thrombolytic agent can also act on the thrombogenic material on the filter bag in addition to acting on the target thrombus. In this manner the occlusive properties of the thrombogenic material on the filter bag may be diminished with time, and blood flow through the filter bag may commensurately increase, which may reestablish perfusion of the downstream vasculature. Because of the time it takes for the thrombolytic agent to dissolve the thrombogenic material on the filter bag, the thrombolytic agent may have more of an opportunity to dissolve the target thrombus.

Figure 9:
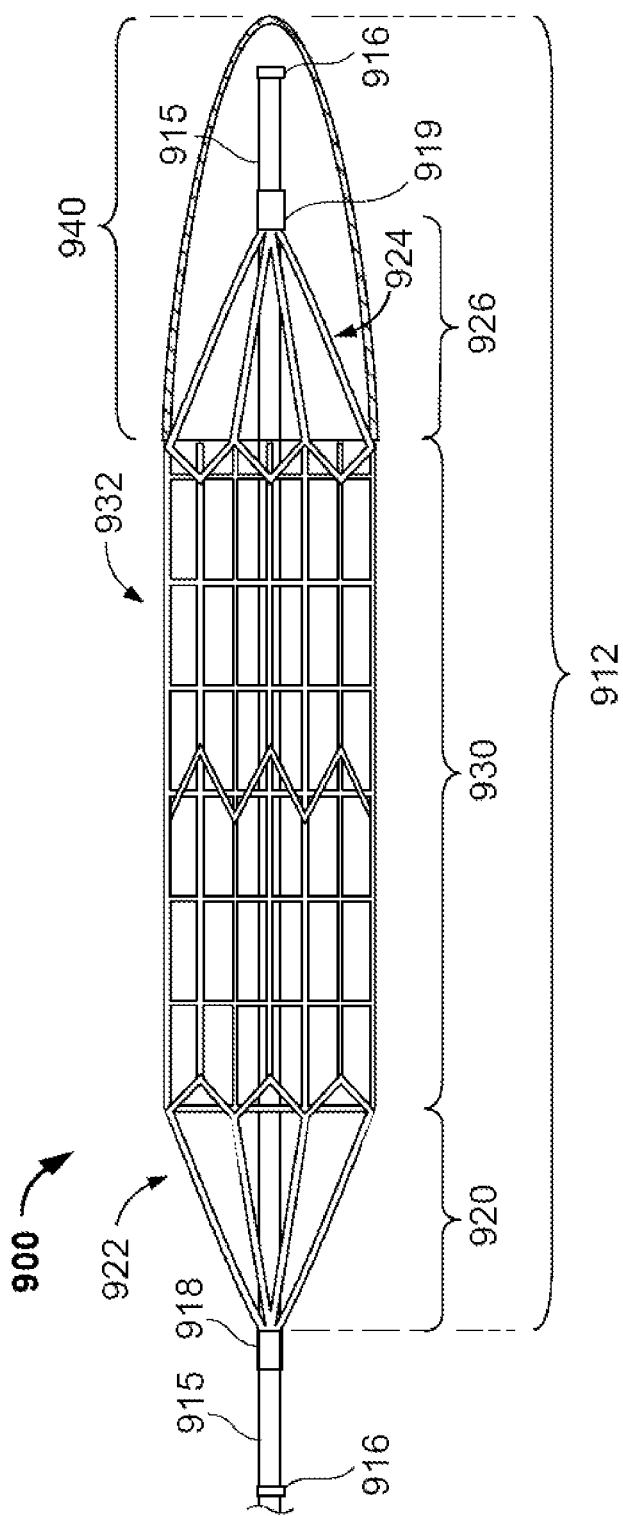
FIG. 9 illustrates another example thrombectomy device.

FIG. 9 illustrates an example embodiment of a thrombectomy device 900. This device can be delivered percutaneously and through a patient's vasculature to the site of a thrombus, such as a neurovascular, cardiovascular, or peripheral vein thrombus site. The thrombectomy device 900 may be used in both antegrade and retrograde applications.

The example thrombectomy device 900 generally includes a support wire 915 and a device body 912 including four (4) primary components: (i) a proximal tether assembly 920, (ii) a body frame 930, (iii) a distal tether assembly 926, and (iv) a filter bag 940 (shown in a cross-sectional view to enable visualization of the distal tether assembly 926 that is located within the internal space defined by the filter bag 940).

A proximal central collar 918 can couple the proximal tether assembly 920 to the support wire 915. A distal central collar 919 can couple the distal tether assembly 926 to the support wire 915. The support wire 915 extends at least between the proximal central collar 918 and the distal central collar 919. In some embodiments, the support wire 915 extends distally beyond the distal central collar 919.

In some embodiments one or both central collars 918 and 919 are movably coupled to the support wire 915. In some embodiments, making one or both central collars 918 and 919 movably coupled to the support wire 915 can facilitate collapsibility of the device 900 for deploying the device 900 via a delivery catheter. In some embodiments, making one or both central collars 918 and 919 movably coupled to the support wire 915 can facilitate eversion of the tether assemblies 920 and 926 for thrombus maceration processes. In some such embodiments, the proximal central collar 918 is fixedly coupled to the support wire 915 and the distal central collar 919 is movably coupled to the support wire 915. In some such embodiments, the proximal central collar 918 is movably coupled to the support wire 915 and the distal central collar 919 is fixedly coupled to the support wire 915. In some such embodiments, the proximal central collar 918 is movably coupled to the support wire 915 and the distal central collar 919 is movably coupled to the support wire 915. In some such embodiments, the proximal central collar 918 is fixedly coupled to the support wire 915 and the distal central collar 919 is fixedly coupled to the support wire 915.

In some embodiments, one or more collar stops 916 are included on the support wire 915. The collar stops 916 can limit the travel of movably coupled central collars 918 and 919.

The distal device body 912 is collapsible so it can be contained within a catheter lumen for delivery through the patient's vasculature to the location of a thrombus (refer, e.g., to FIGS. 2D and 2E). At the thrombus site, the thrombectomy device 900 can be deployed outwardly from the distal tip of the delivery catheter, at which time the thrombectomy device 900 can expand to the unconstrained configuration shown in FIG. 9.

The support wire 915 can include a solid or hollow support wire, or can include any other tubular article with at least one continuous lumen running therethrough (as described above in reference to support wire 15). In some embodiments, support wire 915 extends through the distal end of the filter bag 940 to become the most distal component of the thrombectomy device 900. In some embodiments, support wire 915 extends into the distal device body 912 but not through the distal end of the filter bag 940. In some embodiments, support wire 915 extending distally from at least the body frame 930 can also include one or more balloon devices disposed near the distal end.

The tether assemblies 920 and 926 of the thrombectomy device 900 include one or more tethers 922 and 924 respectively. The one or more tethers 922 and 924 are generally elongate elements (as described above in reference to tethers 22) that can be coupled on one end with the support wire 915 (using one or more collars, such as central collars 918 and 919). The tethers 922 and 924 can be coupled with the body frame 930 at the tether's 922 and 924 opposite end. In some embodiments, the proximal tethers 922 extend from the support wire 915 to the proximal end of the body frame 930. In some embodiments, the distal tethers 924 extend from the support wire 915 to the distal end of the body frame 930. In some embodiments, the tethers 922 and 924 extend from the support wire 915 to locations on the body frame 930 between the proximal and distal ends of the body frame 930 (not shown). While in some embodiments just one proximal tether 922 is included, some embodiments include two, three, four, or more proximal tethers 922. While in some embodiments just one distal tether 924 is included, some embodiments include two, three, four, or more distal tethers 924.

The length of the tethers 922 and 924 can be determined in accordance with the operational characteristics desired. For example, in some applications a short deployment length is desired, leading to a selection of short or looped support strut tethers 922 and 924. In some applications the ability to evert the tethers 922 and 924 within the body frame 930 or filter bag 940 leads to a selection of using longer tethers 922 and 924, which may also be looped in some examples.

In some embodiments, the tethers 922 and 924 are substantially the same length. In some embodiments, the proximal tethers 922 and the distal tethers 924 have dissimilar lengths. In some embodiments, the tethers 922 and 924 are of substantially equal cross-sectional size and/or shape. In some embodiments, the proximal tethers 922 and the distal tethers 924 have dissimilar cross-sectional sizes and/or shapes in comparison to one another.

In some embodiments, all the proximal tethers 922 are of substantially equal length. In some embodiments, one or more proximal tethers 922 are unequal in length in comparison to one or more other proximal tethers 922. In some embodiments, all the proximal tethers 922 are of substantially equal cross-sectional size and/or shape. In some embodiments, one or more proximal tethers 922 are unequal in cross-sectional size and/or shape in comparison to one or more other proximal tethers 922.

In some embodiments, all the distal tethers 924 are of substantially equal length. In some embodiments, one or more distal tethers 924 are unequal in length in comparison to one or more other distal tethers 924. In some embodiments, all the distal tethers 924 are of substantially equal cross-sectional size and/or shape. In some embodiments, one or more distal tethers 924 are unequal in cross-sectional size and/or shape in comparison to one or more other distal tethers 924.

The tethers 922 and 924 can serve multiple purposes. For example, one purpose of the tethers 922 and 924 can be to couple the distal device body 912 of the thrombectomy device 900 to the support wire 915. Another purpose of the tethers 922 and 924 can be to enable flexible compliance between the body frame 930 and the contours of irregularly shaped thrombi or vessel walls. Another purpose can be to provide supplemental radial force between the body frame 930 and a thrombus so as to recanalize or maintain a blood-flow path. Another purpose (as described further above, e.g., FIGS. 2G and 2H) can be to sever, shave, or break up thrombi by everting and causing a pivoting motion (or linear motion) of the tethers 922 and 924 as a part of a thrombectomy procedure. In some implementations, the tethers 922 and 924 need not be everted to sever, shave, or break up thrombi and participate in the thrombectomy procedure. In some implementations, the tethers 922 and 924 may be coated with an abrasive material, which may aid the tethers in severing, shaving, or breaking up thrombi when pivotal motion is applied to the tethers 922 and 924. In some implementations, a portion of the tethers may be sharpened, which may aid the tethers in severing, shaving, or breaking up thrombi when pivotal motion is applied to the tethers 922 and 924.

The body frame 930 can be generally analogous to the body frame 930 (e.g., in reference to FIG. 1). In general, embodiments of the self-expanding body frame 930 can provide a substantial radial force, while exhibiting a minimal lateral resistance to being collapsed to a low profile for placement in a delivery catheter. The radial force can be used to recanalize or maintain a blood-flow path through or around a thrombus. The minimal lateral resistance to being collapsed is useful for positioning and repositioning the body frame 930 within the small diameter of a delivery catheter. Interstices in the body frame 930 provide open spaces between the strut elements 932 that can allow for portions of a thrombus to protrude within the interior of the body frame 930. Portions of thrombus in the interior of the body frame 930 can be removed by, for example, aspiration or maceration (as described above). In some embodiments, the ratio of the length of the body frame 930 to the outer diameter of the body frame 930 in an expanded and unconstrained state is about 1:1, about 2:1, about 3:1, about 4:1, about 5:1, about 6:1, about 7:1, about 8:1, or more than about 8:1.

The filter bag 940 can be generally analogous to the filter bag 940 (e.g., in reference to FIG. 1). In general, filter bag 940 can capture and contain thromboemboli, plaque, and other particulate, while enabling pass-through flow of blood. The filter bag 940 can be made from a variety of filter media materials. For example, the filter media can be a laser perforated layer of thin polytetrafluoroethylene (PTFE). In some embodiments, the range of pore sizes of the filter media can be from 20-30 µm, 30-50 µm, 50-70 µm, 70-80 µm, or 80-100 µm.

In some embodiments, the longitudinal length of the filter bag 940 is approximately proportionate to the length of the body frame 930. For example, in some embodiments the length of the filter bag 940 is less than or equal to about one-half of the length of the body frame 930. In some embodiments, the length of the filter bag 940 is about one-half of the length of the body frame 930 to about equal to the length of the body frame 930. In some embodiments, the length of the filter bag 940 is greater than the length of the body frame 930.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various assemblies and components in the embodiments described above should not be understood as requiring such separation in all embodiments, and it should be understood that the described components and systems can generally be integrated together in a single product or into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A thrombus treatment device, comprising:
a support tube defining a longitudinal axis;
a body frame portion that is disposed about the longitudinal axis defined by the support tube, the body frame portion including a proximal end and a distal end;
a filter portion that extends from the distal end of the body frame portion; and
multiple tethers each having a first end and a second end, wherein the first end of each of the multiple tethers extends out a proximal end of the support tube, the tethers extending through a lumen of the support tube and out a distal end of the support tube and engaging the body frame portion near the distal end of the body frame portion and extending to the proximal end of the body frame portion, the second end of each of the multiple tethers being attached to the body frame portion near the proximal end of the body frame portion, wherein each tether of the multiple tethers forms a loop around the body frame portion near the proximal end of the body frame portion.

2. The thrombus treatment device of claim 1, wherein a longitudinal length of the body frame portion is at least three times as long as an outer diameter of the body frame portion.

3. The thrombus treatment device of claim 1, wherein a longitudinal length of the body frame portion is at least four times as long as an outer diameter of the body frame portion.

4. The thrombus treatment device of claim 1, wherein a longitudinal length of the body frame portion is at least five times as long as an outer diameter of the body frame portion.

5. The thrombus treatment device of claim 1, wherein a longitudinal length of the filter portion is less than or equal to one-half of the longitudinal length of the body frame portion.

6. The thrombus treatment device of claim 1, wherein one or more tethers are comprised of nitinol.

7. The thrombus treatment device of claim 1, wherein one or more tethers are comprised of a polymeric material.

8. The thrombus treatment device of claim 1, wherein the tethers extend from the distal end of the support tube near a central collar that is coupled thereto.

9. The thrombus treatment device of claim 1, wherein the filter portion does not substantially overlap the body frame portion.

10. The thrombus treatment device of claim 1, wherein the body frame portion defines a plurality of open-faced cells arranged in at least three rows along a longitudinal length of the body frame portion, and wherein the filter portion overlaps the body frame portion by up to one row of the at least three rows and does not overlap a remaining body frame portion.

11. The thrombus treatment device of claim 10, wherein the body frame portion defines from three to ten rows of open-faced cells along the longitudinal length of the body frame portion.

12. The thrombus treatment device of claim 1, wherein the filter portion overlaps 20% or less of a longitudinal length of the body frame portion.

13. The thrombus treatment device of claim 1, wherein a proximally directed force applied to the first end of each of the multiple tethers causes the distal end of the body frame portion and the proximal end of the body frame portion to collapse radially toward the longitudinal axis defined by the support tube.

14. A thrombus treatment device, comprising:
a support tube defining a longitudinal axis;
a body frame portion that is disposed about the longitudinal axis defined by the support tube, the body frame portion including a proximal end and a distal end;
a filter portion that extends from the distal end of the body frame portion; and
multiple tethers each having a first end and a second end, wherein the first end of each of the multiple tethers extends out a proximal end of the support tube, the tethers extending through a lumen of the support tube and out a distal end of the support tube and engaging the body frame portion near the distal end of the body frame portion and extending to the proximal end of the body frame portion, the second end of each of the multiple tethers being attached to the body frame portion near the proximal end of the body frame portion, wherein the multiple tethers collectively form a loop around the body frame portion near the proximal end of the body frame portion.

15. The thrombus treatment device of claim 14, wherein a proximally directed force applied to the first end of each of the multiple tethers causes the distal end of the body frame portion and the proximal end of the body frame portion to collapse radially toward the longitudinal axis defined by the support tube.

16. The thrombus treatment device of claim 14, wherein a longitudinal length of the body frame portion is at least three times as long as an outer diameter of the body frame portion.

17. The thrombus treatment device of claim 14, wherein a longitudinal length of the body frame portion is at least four times as long as an outer diameter of the body frame portion.

18. The thrombus treatment device of claim 14, wherein a longitudinal length of the body frame portion is at least five times as long as an outer diameter of the body frame portion.

19. The thrombus treatment device of claim 14, wherein a longitudinal length of the filter portion is less than or equal to one-half of the longitudinal length of the body frame portion.

20. The thrombus treatment device of claim 14, wherein one or more tethers are comprised of nitinol.

21. The thrombus treatment device of claim 14, wherein one or more tethers are comprised of a polymeric material.

22. The thrombus treatment device of claim 14, wherein the tethers extend from the distal end of the support tube near a central collar that is coupled thereto.

23. The thrombus treatment device of claim 14, wherein the filter portion does not substantially overlap the body frame portion.

24. The thrombus treatment device of claim 14, wherein the body frame portion defines a plurality of open-faced cells arranged in at least three rows along a longitudinal length of the body frame portion, and wherein the filter portion overlaps the body frame portion by up to one row of the at least three rows and does not overlap a remaining body frame portion.

25. The thrombus treatment device of claim 24, wherein the body frame portion defines from three to ten rows of open-faced cells along the longitudinal length of the body frame portion.

26. The thrombus treatment device of claim 14, wherein the filter portion overlaps 20% or less of a longitudinal length of the body frame portion.

* * * * *